United States Patent
Imada et al.

(10) Patent No.: US 9,828,457 B2
(45) Date of Patent: Nov. 28, 2017

(54) COMPOUND CONTAINING PHENOLIC HYDROXY GROUP, PHOTOSENSITIVE COMPOSITION, COMPOSITION FOR RESISTS, RESIST COATING FILM, CURABLE COMPOSITION, COMPOSITION FOR RESIST UNDERLAYER FILMS, AND RESIST UNDERLAYER FILM

(71) Applicant: DIC Corporation, Tokyo (JP)

(72) Inventors: Tomoyuki Imada, Ichihara (JP); Yusuke Sato, Ichihara (JP); Seiji Kimoto, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 14/906,050

(22) PCT Filed: Jun. 12, 2014

(86) PCT No.: PCT/JP2014/065573
§ 371 (c)(1),
(2) Date: Jan. 19, 2016

(87) PCT Pub. No.: WO2015/008560
PCT Pub. Date: Jan. 22, 2015

(65) Prior Publication Data
US 2016/0159962 A1   Jun. 9, 2016

(30) Foreign Application Priority Data

Jul. 19, 2013  (JP) .................. 2013-150516
Jul. 19, 2013  (JP) .................. 2013-150517
Aug. 5, 2013   (JP) .................. 2013-162300
Aug. 6, 2013   (JP) .................. 2013-163190
Aug. 6, 2013   (JP) .................. 2013-163193

(51) Int. Cl.
| | | |
|---|---|---|
| G03F 7/004 | (2006.01) | |
| G03F 7/09 | (2006.01) | |
| G03F 7/11 | (2006.01) | |
| C08G 8/20 | (2006.01) | |
| C09D 161/12 | (2006.01) | |
| C07C 39/17 | (2006.01) | |
| G03F 7/022 | (2006.01) | |
| G03F 7/023 | (2006.01) | |
| C08G 8/04 | (2006.01) | |

(52) U.S. Cl.
CPC .............. *C08G 8/20* (2013.01); *C07C 39/17* (2013.01); *C08G 8/04* (2013.01); *C09D 161/12* (2013.01); *G03F 7/004* (2013.01); *G03F 7/0226* (2013.01); *G03F 7/0236* (2013.01); *G03F 7/094* (2013.01); *G03F 7/11* (2013.01); *C07C 2603/92* (2017.05)

(58) Field of Classification Search
None
See application file for complete search history.

(56) References Cited

U.S. PATENT DOCUMENTS

| | | | |
|---|---|---|---|
| 5,166,173 A | 11/1992 | Hwang et al. | |
| 5,196,452 A | 3/1993 | Hwang et al. | |
| 5,302,672 A * | 4/1994 | Ogura et al. ............ | C07C 37/20 525/481 |
| 2010/0028802 A1* | 2/2010 | Konno et al. ........... | G03F 7/091 430/270.1 |

(Continued)

FOREIGN PATENT DOCUMENTS

| | | | |
|---|---|---|---|
| JP | 61-069826 | * | 4/1986 |
| JP | 61-138622 | * | 6/1986 |

(Continued)

OTHER PUBLICATIONS

Li "Synthesis and properties of calix[4]naphthalenes", Thesis, Memorial University of Newfoundland, Canada (Jan. 1996).*
International Search Report and Written Opinion dated Sep. 9, 2014, issued for PCT/JP2014/065573.
First Office Action issued in corresponding Taiwanese Patent Application, dated Jun. 12, 2017.

*Primary Examiner* — Martin Angebranndt
(74) *Attorney, Agent, or Firm* — Locke Lord LLP; James E. Armstrong, IV; Nicholas J. DiCeglie, Jr.

(57) ABSTRACT

Provided is a compound containing a phenolic hydroxy group which has excellent heat resistance, a resist composition which has excellent thermal decomposition resistance, optical sensitivity and resolution, and a composition for a resist underlayer coating which has excellent thermal decomposition resistance and dry etching resistance. The compound containing a phenolic hydroxy group has a molecular structure represented by Structural Formula (1) below:

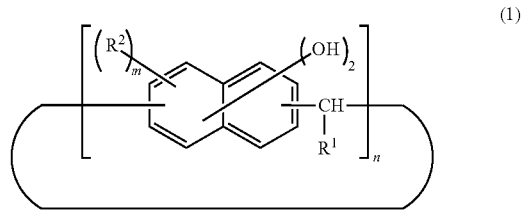

wherein $R^1$ is a hydrogen atom, an alkyl group or an aryl group, n is an integer of 2 to 10, $R^2$ is any one of an alkyl group, an alkoxy group, an aryl group, an aralkyl group and a halogen atom, m is an integer of 0 to 4, and when m is 2 or greater, a plurality of $R^2$'s may be the same as or different from each other and may be bonded to either one of two aromatic rings of the naphthylene skeleton.

12 Claims, 14 Drawing Sheets

(56) References Cited

U.S. PATENT DOCUMENTS

| | | | |
|---|---|---|---|
| 2010/0316950 A1* | 12/2010 | Oguro et al. | G03F 7/094 430/270.1 |
| 2012/0171611 A1* | 7/2012 | Ideno et al. | C08G 10/02 430/270.1 |
| 2012/0285929 A1 | 11/2012 | Matsumura et al. | |
| 2013/0098870 A1* | 4/2013 | Wakamatsu et al. | B44C 1/227 216/49 |
| 2013/0157195 A1* | 6/2013 | Green et al. | C07C 69/753 430/281.1 |
| 2013/0171569 A1 | 7/2013 | Tachibana et al. | |
| 2014/0186776 A1* | 7/2014 | Uchiyama et al. | C09D 161/06 430/323 |
| 2015/0185613 A1* | 7/2015 | Toyokawa | G03F 7/26 438/704 |

FOREIGN PATENT DOCUMENTS

| | | | |
|---|---|---|---|
| JP | 02-189326 | * | 7/1990 |
| JP | 10-239843 | * | 9/1998 |
| JP | 2010-248435 A | | 11/2010 |
| JP | 2012-162474 | * | 8/2012 |
| JP | 2012-162474 A | | 8/2012 |
| JP | 2012-201798 | * | 10/2012 |
| JP | 2012-252323 A | | 12/2012 |
| WO | 2012/165507 | * | 6/2012 |
| WO | 2014/038680 | * | 3/2014 |

* cited by examiner

COMPOUND CONTAINING PHENOLIC HYDROXY GROUP, PHOTOSENSITIVE COMPOSITION, COMPOSITION FOR RESISTS, RESIST COATING FILM, CURABLE COMPOSITION, COMPOSITION FOR RESIST UNDERLAYER FILMS, AND RESIST UNDERLAYER FILM

TECHNICAL FIELD

The present invention relates to a compound containing a phenolic hydroxy group which has excellent heat resistance, a resist composition which has excellent thermal decomposition resistance, optical sensitivity and resolution, and a composition for a resist underlayer which has excellent thermal decomposition resistance and dry etching resistance.

BACKGROUND ART

A compound containing a phenolic hydroxy group is not only used for an adhesive, a molding material, a coating material, a photoresist material, an epoxy resin raw material, or a curing agent for epoxy resin, but is also widely used in the electric and/or electronic field such as a semiconductor sealing material or an insulating material for printed circuit board, as a curable resin composition using the compound containing a phenolic hydroxy group itself as a main agent or as a curing agent for an epoxy resin or the like, since a cured product thereof has excellent heat resistance and moisture resistance.

Among the above, in the field of photoresist, various properties such as alkali solubility, optical sensitivity, and resolution are required in addition to heat resistance. In addition, in a multilayer resist method which has been developed recently as a method for forming a finer wiring pattern, after one or a plurality of layers, which is referred to as a resist underlayer coating or an anti-reflection coating, is formed on a substrate, a resist pattern is formed on the substrate by ordinary photolithography, and then a wiring pattern is transcribed on the substrate by dry etching. One of the important members in the technology of the multilayer resist method is the resist underlayer coating, and as for the underlayer coating, the following characteristics are required: dry etching resistance is high; line edge roughness (LER) of a resist pattern is low; light reflectivity is low; and thermal decomposition resistance is high. In addition, since the resist underlayer coating is prepared in a state of being diluted in a solvent, it is required that a resin material for a resist underlayer coating can be dissolved in general organic solvents, and further, it is required that a resin composition for a resist underlayer coating can be dissolved in an alkali developing solution before curing and can be removed at the same time when a photoresist is developed, depending on an aspect of forming a resist pattern.

As a compound containing a phenolic hydroxy group having excellent heat resistance, a dihydroxynaphthalene type novolac resin (refer to PTL 1), or a compound containing a phenolic hydroxy group having a cylindrical structure which is referred to as a calixarene structure (refer to PTL 2) is known, and as a compound containing a phenolic hydroxy group for a resist underlayer coating, a compound containing a fluorene skeleton having a molecular structure represented by Structural Formula below (refer to PTL 3) is known.

[Chem. 1]

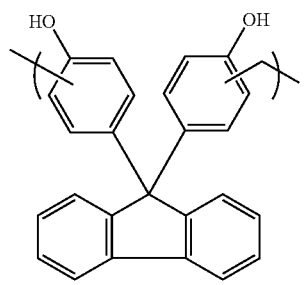

Among the above, the dihydroxynaphthalene type novolac resin disclosed in PTL 1 has excellent heat resistance among general phenol novolac resins, but does not satisfy the level required for heat resistance, which has increased more and more recently, and in a case where the resin is used for a resist, sensitivity or resolution is degraded. Meanwhile, the 1-naphthol type calix(4)arene compound disclosed in PTL 2 does not have sufficient solubility in general organic solvents, and it is difficult to apply the compound to an adhesive, a coating material, a photoresist, and a printed circuit board. In addition, the compound containing a fluorene skeleton disclosed in PTL 3 has excellent solubility in general organic solvents, and exhibits low light reflectivity in terms of a cured coating. However, the compound does not satisfy the recent level required for dry etching resistance and thermal decomposition resistance. Thus, a development of the phenolic compound for a resist underlayer coating having higher dry etching resistance and thermal decomposition resistance is required.

CITATION LIST

Patent Literature

PTL 1: JP-A-2010-248435
PTL 2: JP-A-2012-162474
PTL 3: JP-A-2012-252323

SUMMARY OF INVENTION

Technical Problem

Therefore, an object of the present invention is to provide a compound containing a phenolic hydroxy group, which has excellent heat resistance, a resist composition which has excellent thermal decomposition resistance, optical sensitivity and resolution, and a composition for a resist underlayer coating, which has excellent thermal decomposition resistance and dry etching resistance.

Solution to Problem

As a result of thorough study to solve the problem described above, the present inventors have found that the dihydroxynaphthalene type calixarene compound has remarkably high heat resistance and excellent solubility in general solvents, a positive type resist coating obtained by using the compound has excellent optical sensitivity and resolution, and further, a coating formed of a curable composition using the compound has excellent dry etching resistance and thermal decomposition resistance and low light reflectivity, and the compound is appropriately used for the resist underlayer coating, thereby completing the present invention.

That is, the present invention relates to a compound containing a phenolic hydroxy group having a molecular structure represented by Structural Formula (1) below.

[Chem. 2]

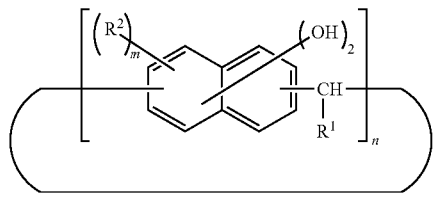

In the formula, $R^1$ is a hydrogen atom, an alkyl group or an aryl group, n is an integer of 2 to 10, $R^2$ is any one of an alkyl group, an alkoxy group, an aryl group, an aralkyl group and a halogen atom, m is an integer of 0 to 4, and when m is 2 or greater, a plurality of $R^2$'s may be the same as or different from each other and may be bonded to either one of two aromatic rings of the naphthylene skeleton.

The present invention further relates to a photosensitive composition including the compound containing a phenolic hydroxy group and a photosensitizer.

The present invention further relates to a resist composition including the photosensitive composition.

The present invention further relates to a resist coating formed by the resist composition.

The present invention further relates to a curable composition including the compound containing a phenolic hydroxy group and a curing agent.

The present invention further relates to a cured product obtained by curing the curable composition.

The present invention further relates to a composition for a resist underlayer coating including the curable composition.

The present invention further relates to a resist underlayer coating formed by the composition for a resist underlayer coating.

Advantageous Effects of Invention

According to the present invention, it is possible to provide a compound containing a phenolic hydroxy group which has excellent heat resistance, a resist composition which has excellent thermal decomposition resistance, optical sensitivity and resolution, and a composition for a resist underlayer coating which has excellent thermal decomposition resistance and dry etching resistance.

DESCRIPTION OF EMBODIMENTS

Figure 1:
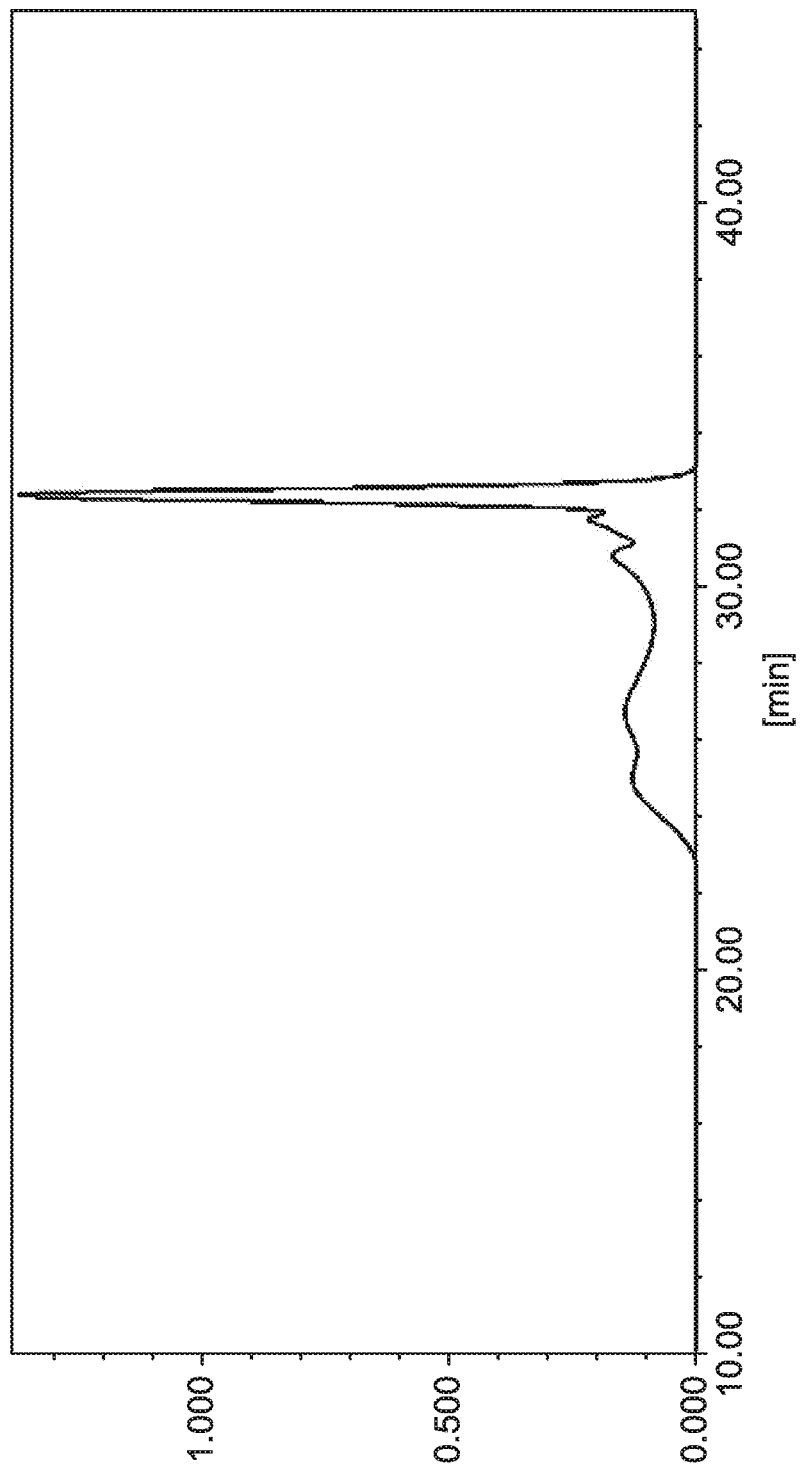
FIG. 1 is a GPC chart of a phenol resin (1) obtained in Example 1.

The compound containing a phenolic hydroxy group of the present invention has a molecular structure represented by Structural Formula (1) below.

[Chem. 3]

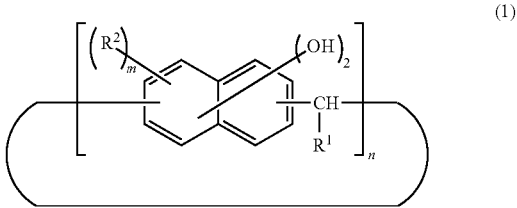

In the formula, $R^1$ is a hydrogen atom, an alkyl group or an aryl group, n is an integer of 2 to 10, $R^2$ is any one of an alkyl group, an alkoxy group, an aryl group, an aralkyl group and a halogen atom, m is an integer of 0 to 4, and when m is 2 or greater, a plurality of $R^2$'s may be the same as or different from each other and may be bonded to either one of two aromatic rings of the naphthylene skeleton.

As described above, a calixarene type compound known in the related art has a high glass transition temperature or a melting point and excellent thermal stability, whereas the compound does not have sufficient compatibility with general organic solvents, other resin components, and additives. In contrast to this, since the compound containing a phenolic hydroxy group represented by Structural Formula (1) above is a compound having two hydroxyl groups on the naphthylene skeleton in Structural Formula (1) above to thereby have a high functional group concentration, the compound has excellent compatibility with general organic solvents, other resin components, and additives, while maintaining high heat resistance which is a characteristic of the calixarene type structure.

Such a compound containing a phenolic hydroxy group has excellent optical sensitivity or resolution, when the compound is used for a photosensitive material. For example, when the compound is used for a positive type resist, a resist coating having high optical sensitivity, which is excellent in both alkali solubility resistance before being exposed to light and alkali solubility after being exposed to light, can be prepared to thereby enable a fine resist pattern to be formed.

In addition, since the compound containing a phenolic hydroxy group represented by Structural Formula (1) above has a calixarene structure including a plurality of naphthalene ring structures, the compound has sufficient rigidity, when the compound is used for a resist underlayer coating, the resist underlayer coating has excellent dry etching resistance in the case of using due to halogen-based plasma gas or the like, and thermal decomposition resistance. Further, since a compound having a plurality of naphthalene ring structures has high refractive index and absorbance, a cured product thereof has low light reflectivity, and is appropriately used as a material for a resist underlayer coating.

n in Structural Formula (1) above represents the number of a repeating unit, and is an integer of 2 to 10. Among the above, in order for the compound containing a phenolic hydroxy group to have excellent structural stability and thermal decomposition resistance, n is preferably any one of 2, 3, 4, 5, 6, and 8, and particularly preferably 4.

A substitution site of two hydroxyl groups on the naphthylene skeleton in Structural Formula (1) above is preferably any one of 1,4 positions, 1,5 positions, 1,6 positions, 2,6 positions, and 2,7 positions, from a viewpoint of easily obtaining a raw material, and more preferably a 1,6 positions, from a viewpoint of manufacturing the compound easily. Specifically, the compound containing a phenolic hydroxy group (A) more preferably has a molecular structure represented by Structural Formula (1-1) below.

[Chem. 4]

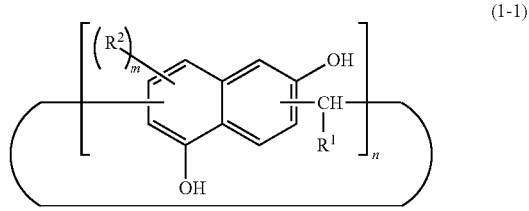

(1-1)

In the formula, $R^1$ is a hydrogen atom, an alkyl group or an aryl group, n is an integer of 2 to 10, $R^2$ is any one of an alkyl group, an alkoxy group, an aryl group, an aralkyl group and a halogen atom, m is an integer of 0 to 4, and when m is 2 or greater, a plurality of $R^2$'s may be the same as or different from each other and may be bonded to either one of two aromatic rings of the naphthylene skeleton.

$R^1$ in Structural Formula (1) above is a hydrogen atom, an alkyl group, or an aryl group, and the examples of the alkyl group include a methyl group, an ethyl group, a propyl group, a butyl group, a pentyl group, a hexyl group, and a cyclohexyl group. In addition, the examples of the aryl group include a structural unit represented by Structural Formulas (2-1) or (2-2) below.

[Chem. 5]

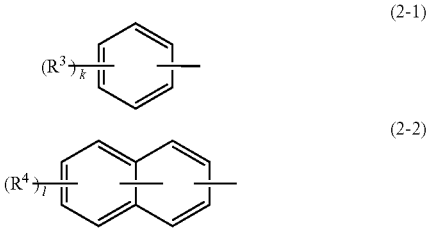

(2-1)

(2-2)

In the formula, $R^3$ and $R^4$ each independently represent any one of a hydroxyl group, a halogen atom, an alkyl group, an alkoxy group, an aryl group and an aralkyl group, k is an integer of 0 to 5, l is an integer of to 7, and when k or l is 2 or greater, a plurality of $R^3$'s or $R^4$'s may be the same as or different from each other.

Examples thereof include a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group.

Among the above, in order for the photosensitive composition to have high sensitivity and resolution and for the compound containing a phenolic hydroxy group to have high dry etching resistance and thermal decomposition resistance, an aryl group is preferable, and a structural unit including a hydroxyl group such as a hydroxyphenyl group, a dihydroxyphenyl group, a hydroxyalkoxyphenyl group, a hydroxynaphthyl group, and a dihydroxynaphthyl group is more preferable.

$R^2$ in Structural Formula (1) above is any one of an alkyl group, an alkoxy group, an aryl group, an aralkyl group, and a halogen atom. Examples of the alkyl group include a methyl group, an ethyl group, a propyl group, a butyl group, a pentyl group, a hexyl group, and a cyclohexyl group, and the examples of the alkoxy group include a methoxy group, an ethoxy group, a propyloxy group, a butoxy group, a pentyloxy group, a hexyloxy group, and a cyclohexyloxy group. In addition, the examples of the aryl group include a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group, and the examples of the aralkyl group include a phenyl methyl group, a hydroxyphenyl methyl group, a dihydroxyphenyl methyl group, a tolyl methyl group, a xylyl methyl group, a naphthyl methyl group, a hydroxynaphthyl methyl group, a dihydroxynaphthyl methyl group, a phenyl ethyl group, a hydroxyphenyl ethyl group, a dihydroxyphenyl ethyl group, a tolyl ethyl group, a xylyl ethyl group, a naphthyl ethyl group, a hydroxynaphthyl ethyl group, and a dihydroxynaphthyl ethyl group.

A value of m in Structural Formula (1) above is preferably 0, in order for the compound containing a phenolic hydroxy group to have excellent thermal decomposition resistance.

The compound containing a phenolic hydroxy group can be prepared by, for example, a method for reacting a dihydroxynaphthalene compound and formaldehyde in the presence of a basic catalyst (method 1), or a method for reacting a dihydroxynaphthalene compound and an aliphatic aldehyde compound having 2 or more carbon atoms or an aromatic aldehyde compound in the presence of an acid catalyst (method 2). In a case where the compound containing a phenolic hydroxy group is prepared by the above methods, the compound containing a phenolic hydroxy group of the present invention can be selectively prepared, or the compound can be prepared as phenol resin composition containing other components, by changing reaction conditions appropriately. In addition, the compound containing a phenolic hydroxy group may be used after isolating the compound from the phenol resin composition including other components.

The method 1 will be described. Examples of the dihydroxynaphthalene compound used in the method 1 include 1,4-dihydroxynaphthalene, 1,5-dihydroxynaphthalene, 1,6-dihydroxynaphthalene, 2,6-dihydroxynaphthalene, 2,7-dihydroxynaphthalene, and a compound obtained by substituting aromatic nuclei of these dihydroxynaphthalenes with one or a plurality of an alkyl group such as a methyl group, an ethyl group, a propyl group, a butyl group, a pentyl group, a hexyl group, and a cyclohexyl group, or an alkoxy group such as a methoxy group, an ethoxy group, a propyloxy group, a butoxy group, a pentyloxy group, a hexyloxy group, and a cyclohexyloxy group. The compound may be used singly or two or more kinds thereof may be used in combination.

Among the dihydroxynaphthalene compounds, 1,6-dihydroxynaphthalene and a compound obtained by substituting an aromatic nucleus of 1,6-dihydroxynaphthalene with one or a plurality of an alkyl group or an aralkyl group are preferable, and 1,6-dihydroxynaphthalene is more preferable, in order to effectively produce the compound containing a phenolic hydroxy group.

The formaldehyde used in the method 1 may be any one of liquid formalin and solid paraformaldehyde.

A reaction ratio of the dihydroxynaphthalene compound to formaldehyde is preferably in a range of 1.0 to 0.1 in terms of a molar ratio [(dihydroxynaphthalene compound)/(formaldehyde)], in order to effectively produce the compound containing a phenolic hydroxy group (A).

In addition, the examples of the basic catalyst used in the method 1 include alkali metal hydroxides such as sodium hydroxide, lithium hydroxide, and potassium hydroxide, and alkaline earth metal hydroxides, such as calcium hydroxide. Among the above, alkali metal hydroxides are preferable since they have high catalytic activity, and sodium hydroxide is more preferable. The use amount of the basic catalyst is preferably in a range of 0.02 moles to 1.00 moles with respect to 1 mole of the dihydroxynaphthalene compound.

When the dihydroxynaphthalene compound is reacted with formaldehyde, the temperature condition is preferably in a range of 60° C. to 90° C., in order to effectively produce the compound containing a phenolic hydroxy group.

A reaction of the dihydroxynaphthalene compound and formaldehyde may be performed in an organic solvent, if necessary. Examples of the organic solvent used in this reaction include alcohol solvents such as propanol, butanol, ethylene glycol, glycerin, ethylene glycol monomethyl ether, ethylene glycol monoethyl ether, ethylene glycol monobutyl ether, and propylene glycol monomethyl ether, and ester solvents such as butyl acetate, ethylene glycol monomethyl ether acetate, ethylene glycol monoethyl ether acetate, and propylene glycol monomethyl ether acetate.

After the reaction of the dihydroxynaphthalene compound and the formaldehyde is completed, the resultant is neutralized by adding an acidic compound in the system, and then cooled, and a crystal of the composition is obtained by filtration, and further washed with water and dried, thereby obtaining a phenol resin composition containing the compound containing a phenolic hydroxy group. Further, if the obtained phenol resin is redissolved in the alcohol solvent or the like and then reprecipitated by adding the resin dropwise to water, it is possible to obtain the compound containing a phenolic hydroxy group with higher purity.

The method 2 will be described. Examples of the dihydroxynaphthalene compound used in the method 2 include 1,4-dihydroxynaphthalene, 1,5-dihydroxynaphthalene, 1,6-dihydroxynaphthalene, 2,6-dihydroxynaphthalene, 2,7-dihydroxynaphthalene, and a compound in which an aromatic nucleus of any one of these dihydroxynaphthalenes is substituted with one or a plurality of an alkyl group such as a methyl group, an ethyl group, a propyl group, a butyl group, a pentyl group, a hexyl group, and a cyclohexyl group, or an alkoxy group such as a methoxy group, an ethoxy group, a propyloxy group, a butoxy group, a pentyloxy group, a hexyloxy group, and a cyclohexyloxy group. The compound may be used singly or two or more kinds thereof may be used in combination.

Among the dihydroxynaphthalene compounds, 1,6-dihydroxynaphthalene and a compound obtained by substituting an aromatic nucleus of 1,6-dihydroxynaphthalene is substituted with two or a plurality of an alkyl group or an aralkyl group is preferable, and 1,6-dihydroxynaphthalene is more preferable, in order to effectively produce the compound containing a phenolic hydroxy group.

Examples of the aliphatic aldehyde compound having 2 or more carbon atoms or the aromatic aldehyde compound used in the method 2 include a compound represented by either one of Structural Formulas (3-1) to (3-3) below.

[Chem. 6]

(3-1)

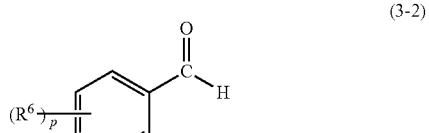

(3-2)

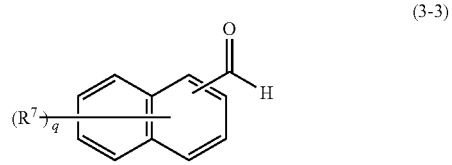

(3-3)

In the formulae, $R^5$ is a hydrocarbon group having 1 to 6 carbon atoms, or a structural unit in which one or a plurality of carbon atoms in the hydrocarbon group is substituted with any one of a hydroxyl group, an alkoxy group, an aryl group and a halogen atom, $R^6$ and $R^7$ each independently represent any one of a hydroxyl group, an alkyl group, an alkoxy group, an aryl group, an aralkyl group and a halogen atom, p is an integer of 0 to 5, q is an integer of 0 to 7, and when p or q is 2 or greater, a plurality of $R^4$'s or $R^5$'s may be the same as or different from each other.

Examples of the aliphatic aldehyde compound represented by Structural Formula (3-1) include acetaldehyde, propyl aldehyde, butyraldehyde, isobutyraldehyde, pentyl aldehyde, and hexyl aldehyde.

Meanwhile, the examples of the aromatic aldehyde compound represented by Structural Formula (3-2) or (3-3) include a hydroxybenzaldehyde compound such as salicylaldehyde, 3-hydroxybenzaldehyde, 4-hydroxybenzaldehyde, 2-hydroxy-4-methyl benzaldehyde, 2,4-dihydroxybenzaldehyde, and 3,4-dihydroxybenzaldehyde; a benzaldehyde compound having both a hydroxy group and an alkoxy group such as 2-hydroxy-3-methoxybenzaldehyde, 3-hydroxy-4-methoxybenzaldehyde, 4-hydroxy-3-methoxybenzaldehyde, 3-ethoxy-4-hydroxybenzaldehyde, and 4-hydroxy-3,5-dimethoxybenzaldehyde; an alkoxybenzaldehyde compound such as methoxybenzaldehyde, and ethoxybenzaldehyde; and a hydroxynaphthaldehyde compound such as 1-hydroxy-2-naphthaldehyde, 2-hydroxy-1-naphthaldehyde, and 6-hydroxy-2-naphthaldehyde. Each of the aldehyde compounds may be used singly, or two or more kinds thereof may be used in combination.

Among the above, in order for the compound containing a phenolic hydroxy group to have high solubility in an organic solvent, high heat resistance, and excellent sensitivity when the compound is made into a photosensitive composition, and to have excellent dry etching resistance and thermal decomposition resistance when the compound is used for a resist underlayer coating, the aromatic aldehyde compound represented by Structural Formula (3-2) or (3-3) is preferable, and a compound having at least one hydroxyl group or at least one alkoxy group as a substituent on aromatic rings, that is, a compound represented by Structural Formulas (3-2) or (3-3) in which p or q is 1 or greater and at least one of $R^6$ and $R^7$ is a hydroxyl group, or a compound represented by Structural Formulas (3-2) or (3-3) in which at least one of $R^6$ and $R^7$ is an alkoxy group, is more preferable. Further, in order to effectively produce the compound containing a phenolic hydroxy group, a hydroxybenzaldehyde compound, which is represented by Structural Formula (y2) in which p is 1 or greater and at least one of $R^6$ is a hydroxyl group, is preferable, any one of 4-hydroxy-3-methoxybenzaldehyde, 3-ethoxy-4-hydroxybenzaldehyde, salicylaldehyde, 3-hydroxybenzaldehyde, 4-hydroxybenzaldehyde, and 2,4-dihydroxybenzaldehyde is more preferable, and any one of salicylaldehyde, 3-hydroxybenzaldehyde, and 4-hydroxybenzaldehyde is particularly preferable.

In the method 2, a reaction ratio of the dihydroxynaphthalene compound to the aldehyde compound is preferably in a range of 0.1 to 3.0 in terms of a molar ratio [(dihydroxynaphthalene compound)/(aldehyde compound)], in order to effectively produce the compound containing a phenolic hydroxy group.

Examples of the acid catalyst used in the method 2 include inorganic acids such as a hydrochloric acid, a sulfuric acid, and a phosphoric acid, organic acids such as a methanesulfonic acid, p-toluenesulfonic acid, and an oxalic acid, and Lewis acids such as boron trifluoride, anhydrous aluminium chloride, and zinc chloride. The use amount of the acid catalyst is preferably in a range of 0.1 mass % to 25 mass % with respect to a total mass of the reaction raw material.

When the dihydroxynaphthalene compound is reacted with the aldehyde compound, the temperature condition is preferably in a range of 50° C. to 120° C., in order to effectively produce the compound containing a phenolic hydroxy group.

A reaction of the dihydroxynaphthalene compound and the aldehyde compound may be performed in an organic solvent, if necessary. Examples of the organic solvent used in this reaction include alcohol solvents such as propanol, butanol, ethylene glycol, glycerin, ethylene glycol monomethyl ether, ethylene glycol monoethyl ether, ethylene glycol monobutyl ether, and propylene glycol monomethyl ether, and ester solvents such as butyl acetate, ethylene glycol monomethyl ether acetate, ethylene glycol monoethyl ether acetate, and propylene glycol monomethyl ether acetate.

After the reaction of the dihydroxynaphthalene compound and the aldehyde compound is completed, a reaction mixture is washed with water, heated to remove the organic solvent under reduced pressure, and dried, thereby obtaining a phenol resin composition containing the compound containing a phenolic hydroxy group. Further, if the obtained phenol resin is redissolved in the alcohol solvent or the like and then reprecipitated by adding the resin dropwise to water, it is possible to obtain the compound containing a phenolic hydroxy group with higher purity.

As described above, since the compound containing a phenolic hydroxy group of the present invention described in detail above has excellent solubility in general organic solvents and thermal decomposition resistance, the compound can be used for an adhesive, a coating material, and various electric and/or electronic members such as a photoresist and a printed circuit board. In particular, the compound containing a phenolic hydroxy group of the present invention is appropriate for a resist, since the compound has excellent alkali solubility, and the compound provides a resist material which has excellent optical sensitivity and resolution. In addition, in a case where the compound containing a phenolic hydroxy group of the present invention is used for a resist underlayer coating, the resist underlayer coating has excellent dry etching resistance, thermal decomposition resistance, and low light reflectivity. In addition, since the compound containing a phenolic hydroxy group of the present invention has a calixarene structure, application of the compound to qualitative or quantitative analysis of metal ions, separation of metal ions, a molecular sensor, an artificial enzyme, a material for various chromatography, or a charge control agent for toner is expected using an inclusion function and a catalytic function caused from the structure.

The photosensitive composition of the present invention includes the compound containing a phenolic hydroxy group of the present invention [hereinafter, shortly referred to as "compound containing a phenolic hydroxy group (A)" and a photosensitizer (B) as an essential component.

Examples of the photosensitizer (B) used in the present invention include a compound having a quinone diazide group. The specific examples of the compound having the quinone diazide group include a complete ester compound or a partial ester compound of an aromatic(poly)hydroxyl compound and sulfonic acids having a quinone diazide group such as naphthoquinone-1,2-diazido-5-sulfonic acid, naphthoquinone-1,2-diazido-4-sulfonic acid, and an ortho-anthraquinone diazido sulfonic acid, an amidated product or a partial amidated product thereof.

Examples of the aromatic(poly)hydroxyl compound used in the above include a polyhydroxybenzophenone compound such as 2,3,4-trihydroxybenzophenone, 2,4,4'-trihydroxybenzophenone, 2,4,6-trihydroxybenzophenone, 2,3,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,3',4,4',6-pentahydroxybenzophenone, 2,2',3,4,4'-pentahydroxybenzophenone, 2,2',3,4,5-pentahydroxybenzophenone, 2,3',4,4',5',6-hexahydroxybenzophenone, and 2,3,3',4,4',5'-hexahydroxybenzophenone;

a bis[(poly)hydroxyphenyl]alkane compound such as bis(2,4-dihydroxyphenyl)methane, bis(2,3,4-trihydroxyphenyl)methane, 2-(4-hydroxyphenyl)-2-(4'-hydroxyphenyl)propane, 2-(2,4-dihydroxyphenyl)-2-(2',4'-dihydroxyphenyl)propane, 2-(2,3,4-trihydroxyphenyl)-2-(2',3',4'-trihydroxyphenyl)propane, 4,4'-{1-[4-[2-(4-hydroxyphenyl)-2-propyl]phenyl]ethylidene}bisphenol, and 3,3'-dimethyl-{1-[4-[2-(3-methyl-4-hydroxyphenyl)-2-propyl]phenyl]ethylidene}bisphenol;

a tris(hydroxyphenyl)methane compound or methyl substitutes thereof such as tris(4-hydroxyphenyl)methane, bis(4-hydroxy-3,5-dimethylphenyl)-4-hydroxyphenylmethane, bis(4-hydroxy-2,5-dimethylphenyl)-4-hydroxyphenylmethane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-2,5-dimethylphenyl)-3,4- dihydroxyphenylmethane, and bis(4-hydroxy-3,5-dimethylphenyl)-3,4-dihydroxyphenylmethane;

a bis(cyclohexylhydroxyphenyl)(hydroxyphenyl)methane compound or methyl substitutes thereof such as bis(3-cyclohexyl-4-hydroxyphenyl)-3-hydroxyphenylmethane, bis(3-cyclohexyl-4-hydroxyphenyl)-2-hydroxyphenylmethane, bis(3-cyclohexyl-4-hydroxyphenyl)-4-hydroxyphenylmethane, bis(5-cyclohexyl-4-hydroxy-2-methylphenyl)-2-hydroxyphenylmethane, bis(5-cyclohexyl-4-hydroxy-2-methylphenyl)-3-hydroxyphenylmethane, bis(5-cyclohexyl-4-hydroxy-2-methylphenyl)-4-hydroxyphenylmethane, bis(3-cyclohexyl-2-hydroxyphenyl)-3-hydroxyphenylmethane, bis(5-cyclohexyl-4-hydroxy-3-methylphenyl)-4-hydroxyphenylmethane, bis(5-cyclohexyl-4-hydroxy-3-methylphenyl)-3-hydroxyphenylmethane, bis(5-cyclohexyl-4-hydroxy-3-methylphenyl)-2-hydroxyphenylmethane, bis(3-cyclohexyl-2-hydroxyphenyl)-4-hydroxyphenylmethane, bis(3-cyclohexyl-2-hydroxyphenyl)-2-hydroxyphenylmethane, bis(5-cyclohexyl-2-hydroxy-4-methylphenyl)-2-hydroxyphenylmethane, and bis(5-cyclohexyl-2-hydroxy-4-methylphenyl)-4-hydroxyphenylmethane. Each of the photosensitizers may be used singly, or two or more kinds thereof may be used in combination.

A blending amount of the photosensitizer (B) in the photosensitive composition of the present invention is preferably 5 parts by mass to 50 parts by mass with respect to 100 parts by mass of the compound containing a phenolic hydroxy group (A), in order for the composition to have excellent optical sensitivity.

The photosensitive composition of the present invention may also include other resins (A') in addition to the compound containing a phenolic hydroxy group (A). As the other resins (A'), any resin which can be dissolved in an alkaline developing agent, or which can be dissolved in an alkaline developing agent when the resin is used in combination with an additive such as an acid generator, can be used.

Examples of the other resins (A') used in the above include other phenol resins (A'-1) other than the compound containing a phenolic hydroxy group (A), a homopolymer or a copolymer of a styrene compound containing a hydroxy group such as p-hydroxystyrene and p-(1,1,1,3,3,3-hexafluoro-2-hydroxypropyl)styrene (A'-2), a compound in which a hydroxyl group of the (A'-1) or (A'-2) is modified with an acid decomposable group such as a t-butoxycarbonyl group and a benzyloxycarbonyl group (A'-3), a homopolymer or a copolymer of a (meth)acrylic acid (A'-4), and an alternating polymer of an alicyclic polymerizable monomer such as a norbornene compound and a tetracyclododecene compound, and maleic anhydride or maleimide (A'-5).

Examples of the other phenol resins (A'-1) include phenol resins such as a phenol novolac resin, a cresol novolac resin, a naphthol novolac resin, a co-condensed novolac resin using various phenolic compounds, an aromatic hydrocarbon formaldehyde resin modified phenol resin, a dicyclopentadiene phenol added resin, a phenol aralkyl resin (ZYLOCK resin), a naphthol aralkyl resin, a trimethylol methane resin, a tetraphenylol ethane resin, a biphenyl modified phenol resin (a polyhydric phenol compound of which phenol nuclei are connected by a bismethylene group), a biphenyl modified naphthol resin (a polyhydric naphthol compound of which phenol nuclei are connected by a bismethylene group), an aminotriazine modified phenol resin (a polyhydric phenol compound of which phenol nuclei are connected by melamine or benzoguanamine), and an alkoxy group containing aromatic ring modified novolac resin (a polyhydric phenol compound of which phenol nuclei and an alkoxy group-containing aromatic ring are connected by formaldehyde).

Among the other phenol resins (A'), a cresol novolac resin or a co-condensed novolac resin of cresol and other phenolic compounds is preferable, in order for the photosensitive resin composition to have high sensitivity and excellent heat resistance. The cresol novolac resin or the co-condensed novolac resin of cresol and other phenolic compounds is a novolac resin obtained by using, specifically, at least one cresol selected from the group consisting of o-cresol, m-cresol and p-cresol and an aldehyde compound as an essential raw material, and arbitrarily using other phenolic compounds in combination.

Examples of other phenolic compounds other than cresol include phenol; xylenol such as 2,3-xylenol, 2,4-xylenol, 2,5-xylenol, 2,6-xylenol, 3,4-xylenol, and 3,5-xylenol; ethylphenol such as o-ethylphenol, m-ethylphenol, p-ethylphenol; isopropylphenol, butylphenol such as butylphenol, p-t-butylphenol; alkylphenol such as p-penthylphenol, p-octylphenol, p-nonylphenol, p-cumylphenol; halogenated phenol such as fluorophenol, chlorophenol, bromophenol, and iodophenol; monosubstituted phenol such as p-phenylphenol, aminophenol, nitrophenol, dinitrophenol, and trinitrophenol; condensed polycyclic phenol such as 1-naphthol, and 2-naphthol; and polyhydric phenol such as resorcin, alkyl resorcin, pyrogallol, catechol, alkyl catechol, hydroquinone, alkyl hydroquinone, phloroglucin, bisphenol A, bisphenol F, bisphenol S, and dihydroxynaphthalene. Each of other phenolic compounds may be used singly, or two or more kinds thereof may be used in combination. In a case where other phenolic compounds are used, the use amount of other phenolic compounds is preferably in a range of 0.05 moles to 1 mole with respect to a total of 1 mole of the cresol raw material.

In addition, examples of the aldehyde compound include formaldehyde, paraformaldehyde, trioxane, acetaldehyde, propionaldehyde, polyoxymethylene, chloral, hexamethylene tetramine, furfural, glyoxal, n-butyraldehyde, caproaldehyde, allylaldehyde, benzaldehyde, crotonaldehyde, acrolein, tetraoxymethylene, phenylacetaldehyde, o-tolualdehyde, and salicylaldehyde. Each of the aldehyde compounds may be used singly, or two or more kinds thereof may be used in combination. Among the above, formaldehyde is preferable since formaldehyde has excellent reactivity, and formaldehyde and other aldehyde compounds may be used in combination. In a case where formaldehyde and other aldehyde compounds are used in combination, the use amount of other aldehyde compounds is preferably in a range of 0.05 moles to 1 mole with respect to 1 mole of formaldehyde.

With regard to a reaction ratio of the phenolic compound to the aldehyde compound when manufacturing the novolac resin, the aldehyde compound is preferably in a range of 0.3 moles to 1.6 moles with respect to 1 mole of the phenolic compound, and more preferably in a range of 0.5 to 1.3, in order for the photosensitive resin composition to have excellent sensitivity and heat resistance.

A reaction of the phenolic compound and the aldehyde compound is performed at a temperature of 60° C. to 140° C. in the presence of the acid catalyst, and then water or residual monomer is removed under reduced pressure. Examples of the acid catalyst used in the above include an oxalic acid, a sulfuric acid, a hydrochloric acid, a phenol sulfonic acid, a paratoluene sulfonic acid, zinc acetate, and manganese acetate, and each of the acid catalysts may be used singly, or two or more kinds thereof may be used in combination. Among the above, oxalic acid is preferable since oxalic acid has excellent catalytic activity.

Among the cresol novolac resin, or the co-condensed novolac resin of cresol and other phenolic compounds described in detail above, a cresol novolac resin using metacresol singly, or a cresol novolac resin using metacresol and paracresol in combination is preferable. In addition, in a case of the latter, a reaction molar ratio of metacresol to paracresol [metacresol/paracresol] is preferably in a range of 10/0 to 2/8, and more preferably 7/3 to 2/8, in order for the photosensitive resin composition to have excellent balance of sensitivity and heat resistance.

In a case where the other resins (A') are used, a blending ratio of the compound containing a phenolic hydroxy group (A) to the other resins (A') may be arbitrarily adjusted according to the desired purpose. For example, a photosensitive composition including the compound containing a phenolic hydroxy group (A) as a main component is appropriate for the resist, since the composition exhibits excellent optical sensitivity, resolution, and heat resistance when the compound is combined with a photosensitizer. At this time, a ratio of the compound containing a phenolic hydroxy group (A) to a total resin component is preferably 60 mass % or more, and more preferably 80 mass % or more, in order for the photosensitive composition to be a curable composition having high optical sensitivity and excellent resolution and heat resistance.

In addition, the compound containing a phenolic hydroxy group (A) may be used as a sensitivity improver by utilizing a characteristic that the compound exhibits excellent optical sensitivity. In this case, a blending ratio of the compound containing a phenolic hydroxy group (A) to the other resins (A') is preferably in a range of 3 parts by mass to 80 parts by mass of the compound containing a phenolic hydroxy group (A) with respect to 100 parts by mass of other resins (A').

In a case where the other resins (A') are used, a blending amount of the photosensitizer (B) in the photosensitive composition of the present invention is preferably 5 parts by mass to 50 parts by mass with respect to a total 100 parts by mass of the resin component in the composition, in order for the photosensitive composition to have excellent optical sensitivity.

The photosensitive composition of the present invention may include a surfactant for the purpose of improving film forming properties or pattern adhesiveness, and reducing development defects when the composition is used for the resist. Examples of the surfactant used in the above include nonionic surfactants such as a polyoxyethylene alkyl ether compound such as polyoxyethylene lauryl ether, polyoxyethylene stearyl ether, polyoxyethylene cetyl ether, and polyoxyethylene oleyl ether, a polyoxyethylene alkyl allyl ether compound such as polyoxyethylene octyl phenol ether and polyoxyethylene nonyl phenol ether, a polyoxyethylene.polyoxypropylene block copolymer, a sorbitan fatty acid ester compound such as sorbitan monolaurate, sorbitan monopalmitate, sorbitan monostearate, sorbitan monooleate, sorbitan trioleate, and sorbitan tristearate, and a polyoxyethylene sorbitan fatty acid ester compound such as polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate; a fluorine-based surfactant having a fluorine atom in a molecular structure such a copolymer of a polymerizable monomer having a fluoro aliphatic group and [poly(oxyalkylene)](meth)acrylate; and a silicone-based surfactant having a silicone structural unit in a molecular structure. Each of the surfactants may be used singly, or two or more kinds thereof may be used in combination.

A blending amount of the surfactant is preferably in a range of 0.001 parts by mass to 2 parts by mass with respect to 100 parts by mass of a resin solid content in the curable composition of the present invention.

In a case where the photosensitive composition of the present invention is used for a photoresist, a resist composition can be prepared by adding various additives such as the other phenol resins (A'), a surfactant, a dye, a filler, a crosslinking agent, and a dissolution accelerator, if necessary, in addition to the compound containing a phenolic hydroxy group (A) and the photosensitizer (B), and dissolving the resulting composition in an organic solvent. The resist composition may be used as a positive type resist solution as it is, or the resist composition may be used as a positive type resist coating by applying the composition in a film shape and removing a solvent. When the composition is used as a resist coating, examples of the supporting film include a synthetic resin film such as polyethylene, polypropylene, polycarbonate, and polyethylene terephthalate, and the film may be a single layer film or a laminated film composed of plural layers. In addition, the surface of the supporting film may be corona treated, or coated with a peeling agent.

The organic solvent used in the resist composition of the present invention is not particularly limited, and the examples thereof include alkylene glycol monoalkyl ether such as ethylene glycol monomethyl ether, ethylene glycol monoethyl ether, ethylene glycol monopropyl ether, ethylene glycol monobutyl ether, and propylene glycol monomethyl ether; dialkylene glycol dialkyl ether such as diethylene glycol dimethyl ether, diethylene glycol diethyl ether, diethylene glycol dipropyl ether, and diethylene glycol dibutyl ether; alkylene glycol alkyl ether acetate such as ethylene glycol monomethyl ether acetate, ethylene glycol monoethyl ether acetate, propylene glycol monomethyl ether acetate; a ketone compound such as acetone, methyl ethyl ketone, cyclohexanone, and methyl amyl ketone; cyclic ether such as dioxane; and an ester compound such as 2-hydroxy methylpropionate, 2-hydroxy ethylpropionate, 2-hydroxy-2-methyl ethyl propionate, ethyl ethoxyacetate, ethyl oxyacetate, 2-hydroxy-3-methyl methylbutanate, 3-methoxybutyl acetate, 3-methyl-3-methoxybutyl acetate, ethyl formate, ethyl acetate, butyl acetate, methyl acetoacetate, and ethyl acetoacetate. Each of the solvents may be used singly, or two or more kinds thereof may be used in combination.

The resist composition of the present invention can be prepared by blending respective components described above and mixing the components using a stirrer or the like. In addition, in a case where the resin composition for photoresist contains a filler or a pigment, the composition can be prepared by dispersing or mixing the materials using a dispersion device such as a dissolver, a homogenizer, and a triple roll mill.

According to the photolithography method using the resist composition of the present invention, for example, the resist composition is applied to a target object such as a silicon substrate on which photolithography is to be performed, and prebaked at a temperature condition of 60° C. to 150° C. The application method may be any method such as spin coating, roll coating, flow coating, dip coating, spray coating, and doctor blade coating. Next, a resist pattern is formed. Since the resist composition of the present invention is a positive type, a target resist pattern is exposed to light through a predetermined mask, and the part exposed to light is dissolved in an alkaline developing solution to form a resist pattern. Since the resist composition of the present invention shows high alkali solubility in the part exposed to light, and also shows high alkali solubility resistance in the part unexposed to light, the resist pattern having excellent resolution can be formed.

A curable composition of the present invention includes the compound containing a phenolic hydroxy group (A) and a curing agent (B) as an essential component.

Examples of the curing agent (B) used in the present invention include a melamine compound which is substituted with at least one group selected from a methylol group, an alkoxy methyl group, an acyloxy methyl group, a guanamine compound, a glycoluril compound, an urea compound, a resol resin, an epoxy compound, an isocyanate compound, an azide compound, a compound having a double bond such as an alkenyl ether group, acid anhydride, and an oxazoline compound.

Examples of the melamine compound include a compound in which 1 to 6 methylol groups of hexamethylol melamine, hexamethoxymethyl melamine, and hexamethylol melamine are methoxymethylated, and a compound in which 1 to 6 methylol groups of hexamethoxyethyl melamine, hexaacyloxymethyl melamine, and hexamethylolmelamine are acyloxymethylated.

Examples of the guanamine compound include a compound in which 1 to 4 methylol groups of tetramethylol guanamine, tetramethoxymethyl guanamine, tetramethoxymethyl benzoguanamine, and tetramethylol guanamine are methoxymethylated, tetramethoxyethyl guanamine, tetraacyloxy guanamine, and a compound in which 1 to 4 methylol groups of tetramethylol guanamine are acyloxymethylated.

Examples of the glycoluril compound include 1,3,4,6-tetrakis(methoxymethyl)glycoluril, 1,3,4,6-tetrakis(butoxymethyl)glycoluril, and 1,3,4,6-tetrakis(hydroxymethyl) glycoluril.

Examples of the urea compound include 1,3-bis(hydroxymethyl)urea, 1,1,3,3-tetrakis(butoxymethyl)urea, and 1,1,3,3-tetrakis(methoxymethyl)urea.

Examples of the resol resin include a polymer obtained by reacting an aldehyde compound with phenol, alkyl phenol such as cresol and xylenol, phenylphenol, resorcinol, biphenyl, bisphenol such as bisphenol A and bisphenol F, or a compound containing a phenolic hydroxy group such as naphthol and dihydroxynaphthalene in the presence of an alkali catalyst.

Examples of the epoxy compound include tris(2,3-epoxypropyl)isocyanurate, trimethylolmethane triglycidyl ether, trimethylolpropane triglycidyl ether, and triethylolethane triglycidyl ether.

Examples of the isocyanate compound include tolylene diisocyanate, diphenylmethane diisocyanate, hexamethylene diisocyanate, and cyclohexane diisocyanate.

Examples of the azide compound include 1,1'-biphenyl-4,4'-bisazide, 4,4'-methylidene bisazide, and 4,4'-oxybisazide.

Examples of the compound having a double bond such as an alkenyl ether group include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

Examples of the acid anhydride include aromatic anhydride such as phthalic anhydride, trimellitic anhydride, pyromellitic anhydride, 3,3',4,4'-benzophenone tetracarboxylic dianhydride, biphenyl tetracarboxylic dianhydride, 4,4'-(isopropylidene)diphthalic anhydride, and 4,4'-(hexafluoroisopropylidene)diphthalic anhydride; and alicyclic carboxylic anhydride such as tetrahydrophthalic anhydride, methyltetrahydrophthalic anhydride, hexahydrophthalic anhydride, methylhexahydrophthalic anhydride, endomethylene tetrahydrophthalic anhydride, dodecenyl succinic anhydride, and trialkyl tetrahydrophthalic anhydride.

Among the above, the glycoluril compound, the urea compound, and the resol resin are preferable, and the glycoluril compound is particularly preferable, in order for the curable composition to exhibit excellent curing properties and excellent dry etching resistance and thermal decomposition resistance when used for a resist underlayer coating.

A blending amount of the curing agent (B) in the curable composition of the present invention is preferably 0.5 parts by mass to 20 parts by mass with respect to 100 parts by mass of the compound containing a phenolic hydroxy group (A), in order for the curing composition to have excellent curing properties.

The curable composition of the present invention may include the other resins in addition to the compound containing a phenolic hydroxy group (A). Examples of the other resins used in the above include various novolac resins, an addition polymerization resin of an alicyclic diene compound such as dicyclopentadiene and a phenol compound, a modified novolac resin of a compound containing a phenolic hydroxy group and an aromatic compound containing an alkoxy group, a phenol aralkyl resin (ZYLOCK resin), a naphthol aralkyl resin, a trimethylolmethane resin, a tetraphenylol ethane resin, a biphenyl modified phenol resin, a biphenyl modified naphthol resin, aminotriazine modified phenol resin, and various vinyl polymers.

The specific examples of the various novolac resins include a polymer obtained by reacting an aldehyde compound with phenol, alkyl phenol such as cresol and xylenol, phenylphenol, resorcinol, biphenyl, bisphenol such as bisphenol A and bisphenol F, or a compound containing a phenolic hydroxy group such as naphthol and dihydroxynaphthalene in the presence of an acid catalyst.

Examples of the various vinyl polymers include a homopolymer or a copolymer of a vinyl compound such as polyhydroxystyrene, polystyrene, polyvinylnaphthalene, polyvinylanthracene, polyvinylcarbazole, polyindene, polyacenaphthylene, polynorbornene, polycyclodecene, polytetracyclododecene, polynortricyclene, and poly(meth)acrylate.

In a case where the other resins are used, a blending ratio of the other resins to the compound containing a phenolic hydroxy group (A) may be arbitrarily set according to the purpose. However, a ratio of the other resins is preferably 0.5 parts by mass to 100 parts by mass with respect to 100 parts by mass of the compound containing a phenolic hydroxy group (A), in order to more remarkably exhibit an effect of the present invention which provides excellence in dry etching resistance and thermal decomposition resistance.

In addition, in a case where the other resins are used, a blending amount of the curing agent (B) in the curable composition of the present invention is preferably 0.5 parts by mass to 50 parts by mass with respect to a total 100 parts by mass of the compound containing a phenolic hydroxy group (A) and other resins, in order for the curable composition to have excellent curing properties.

In a case where the curable composition of the present invention is used for a resist underlayer coating (BARC), a composition for a resist underlayer coating can be prepared by adding the other resins, various additives such as a surfactant, a dye, a filler, a crosslinking agent, and a dissolution accelerator, if necessary, in addition to the compound containing a phenolic hydroxy group (A) and the curing (B), and dissolving the composition in an organic solvent.

The organic solvent used in the composition for a resist underlayer coating is not particularly limited, and the examples thereof include alkylene glycol monoalkyl ether such as ethylene glycol monomethyl ether, ethylene glycol monoethyl ether, ethylene glycol monopropyl ether, ethylene glycol monobutyl ether, and propylene glycol monomethyl ether; dialkylene glycol dialkyl ether such as diethylene glycol dimethyl ether, diethylene glycol diethyl ether, diethylene glycol dipropyl ether, and diethylene glycol dibutyl ether; alkylene glycol alkyl ether acetate such as ethylene glycol monomethyl ether acetate, ethylene glycol monoethyl ether acetate, propylene glycol monomethyl ether acetate; a ketone compound such as acetone, methyl ethyl ketone, cyclohexanone, and methyl amyl ketone; cyclic ether such as dioxane; and an ester compound such as 2-hydroxy propionic acid methyl, 2-hydroxy propionic acid ethyl, 2-hydroxy-2-methyl propionic acid ethyl, ethoxyacetic acid ethyl, oxyacetic acid ethyl, 2-hydroxy-3-methyl butanoic acid methyl, 3-methoxybutyl acetate, 3-methyl-3-methoxybutyl acetate, formic acid ethyl, acetic acid ethyl, butyl acetate, acetoacetic acid methyl, and acetoacetic acid ethyl. Each of the solvents may be used singly, or two or more kinds thereof may be used in combination.

The composition for a resist underlayer coating of the present invention can be prepared by blending respective components described above and mixing the components using a stirrer or the like. In addition, in a case where the composition for a resist underlayer coating contains a filler or a pigment, the composition can be prepared by dispersing or mixing the components using a dispersion device such as a dissolver, a homogenizer, and a triple roll mill.

In order to prepare a resist underlayer coating using the composition for a resist underlayer coating of the present invention, a resist underlayer coating is formed by, for example, a method in which the composition for a resist underlayer coating is applied to a target object such as a silicon substrate on which photolithography is to be performed, and dried at a temperature condition of 100° C. to 200° C., and then further heated and cured at a temperature condition of 250° C. to 400° C. Next, a ordinary photolithography operation is performed on this underlayer coating to form a resist pattern, and the coating is subjected to dry etching with halogen-based plasma gas, thereby forming a resist pattern by a multilayer resist method. Since a coating formed of the curable composition of the present invention has excellent etching resistance and low light reflectivity, it is possible to use the coating for a resist underlayer coating.

EXAMPLES

Next, the present invention will be described specifically using Examples and Comparative Examples, and "parts" and "%" below are based on mass unless otherwise specifically indicated. GPC, 1H-NMR, 13C-NMR, and FD-MS spectrum were measured under the following conditions.
<Measurement Conditions of GPC>
Measuring apparatus: "HLC-8220 GPC" manufactured by Tosoh Corporation,
Column: guard column "HHR-H" (6.0 mm I.D.×4 cm) manufactured by Tosoh Corporation
"TSK-GEL GMHHR-N" (7.8 mm I.D.×30 cm) manufactured by Tosoh Corporation
"TSK-GEL GMHHR-N" (7.8 mm I.D.×30 cm) manufactured by Tosoh Corporation
"TSK-GEL GMHHR-N" (7.8 mm I.D.×30 cm) manufactured by Tosoh Corporation
Detector: ELSD ("ELSD2000" manufactured by Alltech, Inc.)
Data processing: "GPC-8020 model II data analysis Version 4.30" manufactured by Tosoh Corporation
Measurement conditions: Column temperature 40° C.
Developing solvent tetrahydrofuran (THF)
Flow rate 1.0 ml/min
Sample: a solution (5 μl) obtained by filtering a tetrahydrofuran solution of 1.0 mass % in terms of resin solid content through a microfilter.
Standard sample: according to the measurement manual of the "GPC-8020 model II data analysis Version 4.30", the following monodisperse polystyrene of which the molecular weight is known was used.
(Monodisperse Polystyrene)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
"F-288" manufactured by Tosoh Corporation
"F-550" manufactured by Tosoh Corporation
<Measurement Conditions of 1H-NMR and 13C-NMR>
1H-NMR and 13C-NMR were measured under the following conditions.
Apparatus: AL-400 manufactured by JEOL Ltd.
Solvent: dimethylsulfoxide-d6, TMS basis
Sample concentration: 30 wt %
Measurement mode: SGNNE (1H complete decoupling method of NOE elimination)
Pulse angle: 450 pulse
Cumulated number: 10,000 times
<Measurement Conditions of FD-MS Spectrum>
FD-MS spectrum was measured using a double focusing mass spectrometer "AX505H (FD505H)" manufactured by JEOL Ltd.

Example 1 Preparation of Phenol Resin (1)

Figure 2:
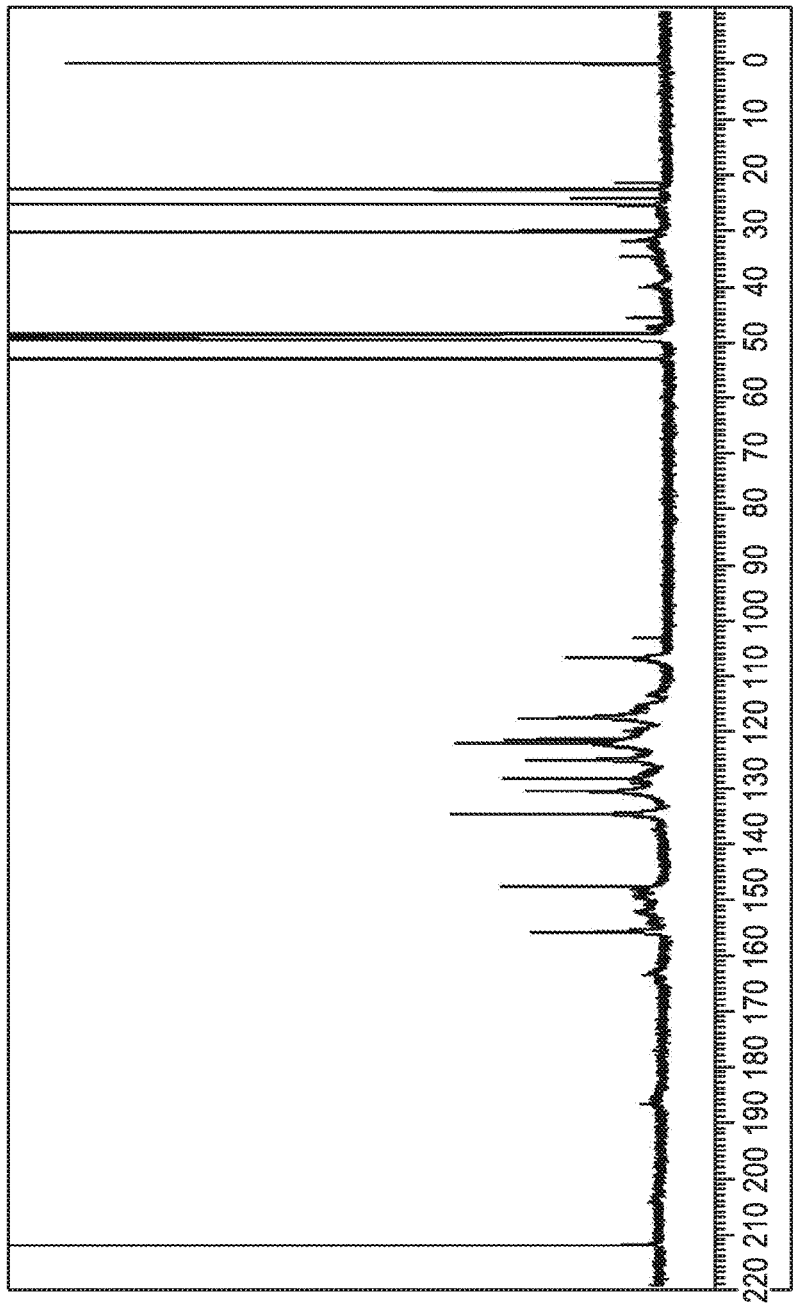
FIG. 2 is a 13C-NMR chart of the phenol resin (1) obtained in Example 1.
Figure 3:
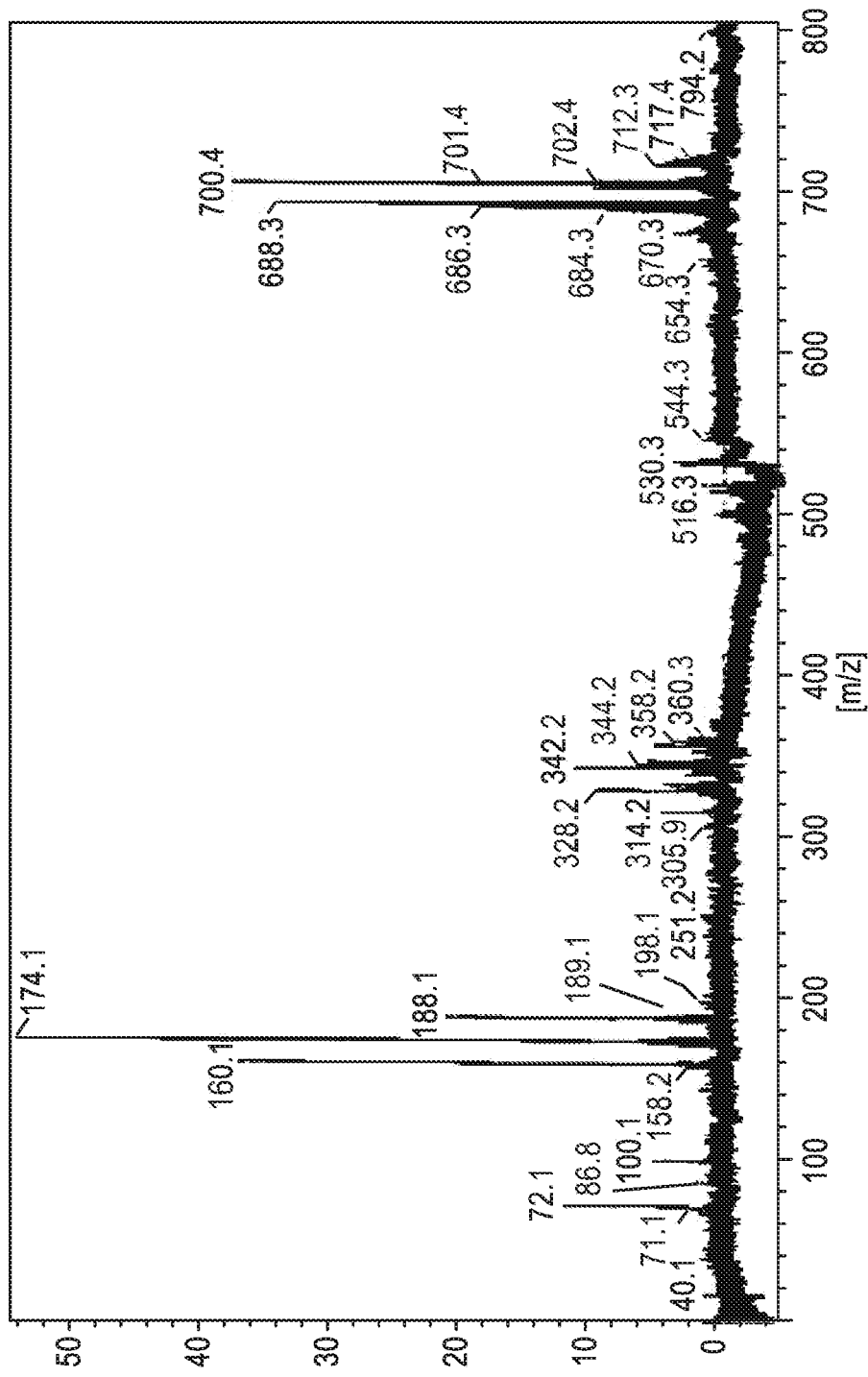
FIG. 3 is a MS spectrum of the phenol resin (1) obtained in Example 1.

48 parts by mass (0.30 moles) of 1,6-dihydroxynaphthalene, 26 parts by mass (0.36 moles) of 42 mass % formaldehyde aqueous solution, 50 parts by mass of isopropyl alcohol, and 12.8 parts by mass (0.11 moles) of 48% potassium hydroxide were put into a flask equipped with a thermometer, a dropping funnel, a cooling tube, and a stirrer, and stirred at room temperature while blowing nitrogen therein. After that, the resultant was heated to a temperature of 80° C. and stirred for 1 hour. After the reaction was completed, the resultant was neutralized by adding 8 parts by mass of primary sodium phosphate, and then cooled and a crystal was filtered out. After the filtered crystal was washed with 50 parts by mass of water 3 times, the crystal was heated and dried under reduced pressure, thereby obtaining 20 parts by mass of a phenol resin (1). A GPC chart of the phenol resin (1) is shown in FIG. 1, a 13C-NMR chart is shown in FIG. 2, and MS spectrum is shown in FIG. 3. A peak of 688 corresponding to the compound containing a phenolic hydroxy group represented by Structural Formula (i) below was detected from MS spectrum. In addition, the content of the compound containing a phenolic hydroxy group (I) represented by Structural Formula (i) below in the phenol resin (1) was 36%, which is calculated from the GPC chart.

In addition, in the Example, the content of the compound containing a phenolic hydroxy group in the phenol resin is a value obtained by calculating existing proportion of the peak area of the compound containing a phenolic hydroxy group with respect to a total peak area of the phenol resin, which is calculated by GPC measurement under the conditions described above.

[Chem. 7]

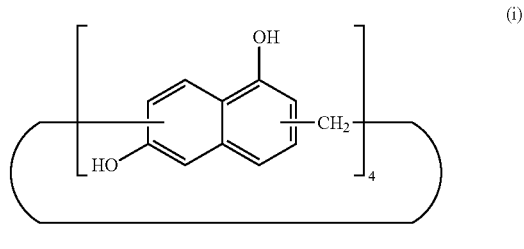

(i)

Example 2 Preparation of Phenol Resin (2)

19 parts by mass of a phenol resin (2) was obtained in the same manner as in Example 1 except that 9.4 parts by mass (0.11 moles) of sodium hydroxide was used instead of 12.8 parts by mass (0.11 moles) of 48% potassium hydroxide in Preparation Example 1. A peak of 688 corresponding to the compound containing a phenolic hydroxy group (I) represented by Structural Formula (i) above was detected from MS spectrum of the phenol resin (2). In addition, the content of the compound containing a phenolic hydroxy group (I) represented by Structural Formula (i) above in the phenol resin (2) was 36%, which is calculated from GPC the chart.

Example 3 Preparation of Phenol Resin (3)

17 parts by mass of a phenol resin (3) was obtained in the same manner as in Preparation Example 1 except that 11.8 parts by mass (0.36 moles) of 92% paraformaldehyde was used instead of 26 parts by mass (0.36 moles) of 42 mass % formaldehyde aqueous solution in Preparation Example 1. A peak of 688 corresponding to the compound containing a phenolic hydroxy group (I) represented by Structural Formula (i) above was detected from MS spectrum of the phenol resin (3). In addition, the content of the compound containing a phenolic hydroxy group (I) represented by Structural Formula (i) above in the phenol resin (3) was 33%, which is calculated from the GPC chart.

Example 4 Preparation of Phenol Resin (4)

Figure 4:
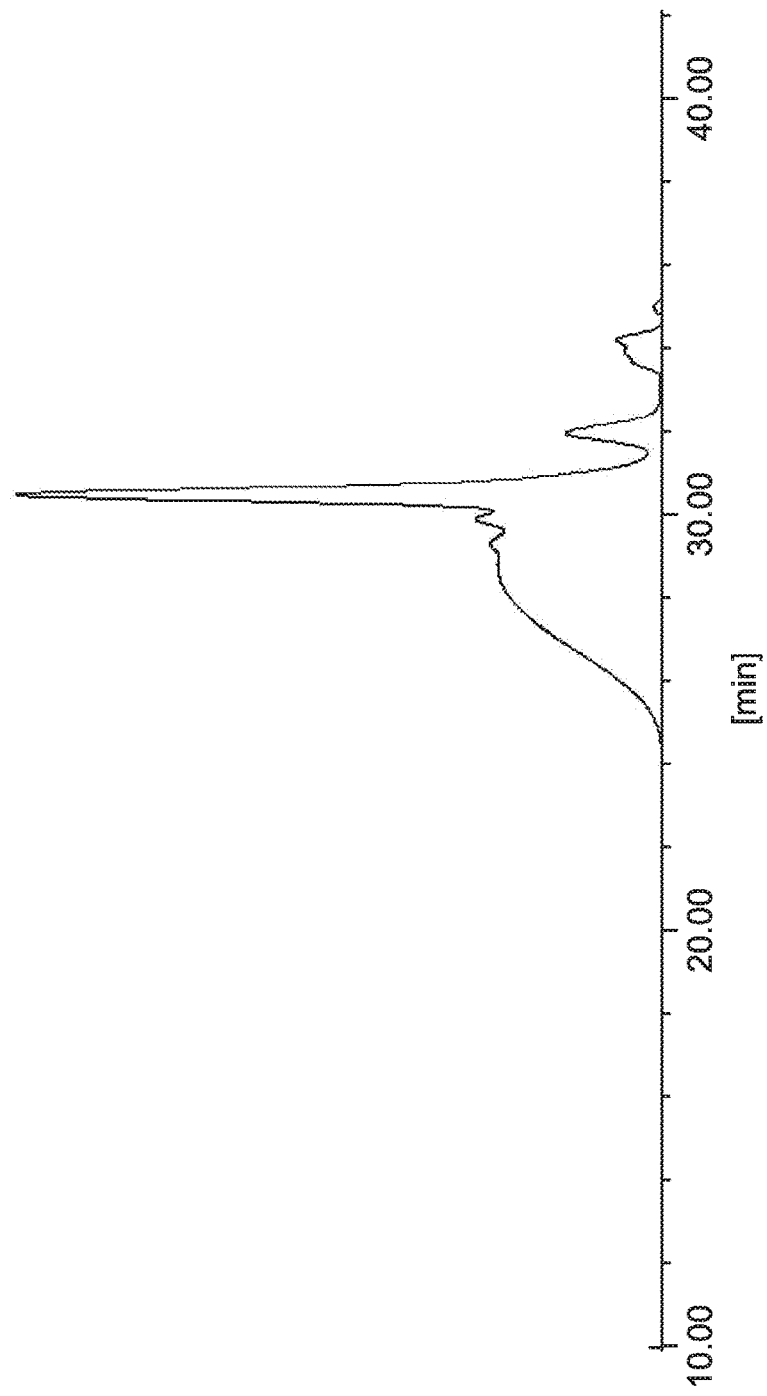
FIG. 4 is a GPC chart of a phenol resin (4) obtained in Example 2.

160 parts by mass of 1,6-dihydroxynaphthalene, 44 parts by mass of paraldehyde, 320 parts by mass of 2-ethoxyethanol, and 1.6 parts by mass of 95% sulfuric acid were put into a flask equipped with a thermometer, a dropping funnel, a cooling tube, and a stirrer, and the resultant was heated to a temperature of 80° C., and then stirred for 8 hours. After the reaction was completed, 300 parts by mass of ethyl acetate and 160 parts by mass of ion exchanged water were added thereto, and then an aqueous layer having pH of 1 was separated from the underlayer by a separating funnel. An organic layer was washed with 160 parts by mass of ion exchanged water 7 times, and it was confirmed that pH of the separated aqueous layer was 4. After the organic layer was concentrated by heating under reduced pressure using an evaporator, the organic layer was dried, thereby obtaining 174 parts by mass of a phenol resin (4) (yield of 94 mass %). A GPC chart of the phenol resin (4) is shown in FIG. 4. A peak of 744 corresponding to the compound containing a phenolic hydroxy group (II) represented by Structural Formula (ii) below was detected from MS spectrum of the phenol resin (4). In addition, the content of the compound containing a phenolic hydroxy group (II) represented by Structural Formula (ii) below in the phenol resin (4) was 34%, which is calculated from the GPC chart.

[Chem. 8]

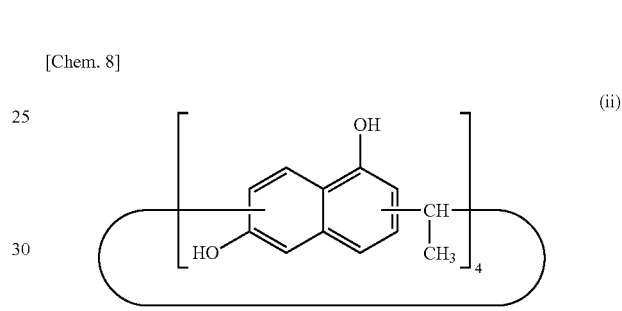

(ii)

Example 5 Preparation of Phenol Resin (5)

Figure 5:
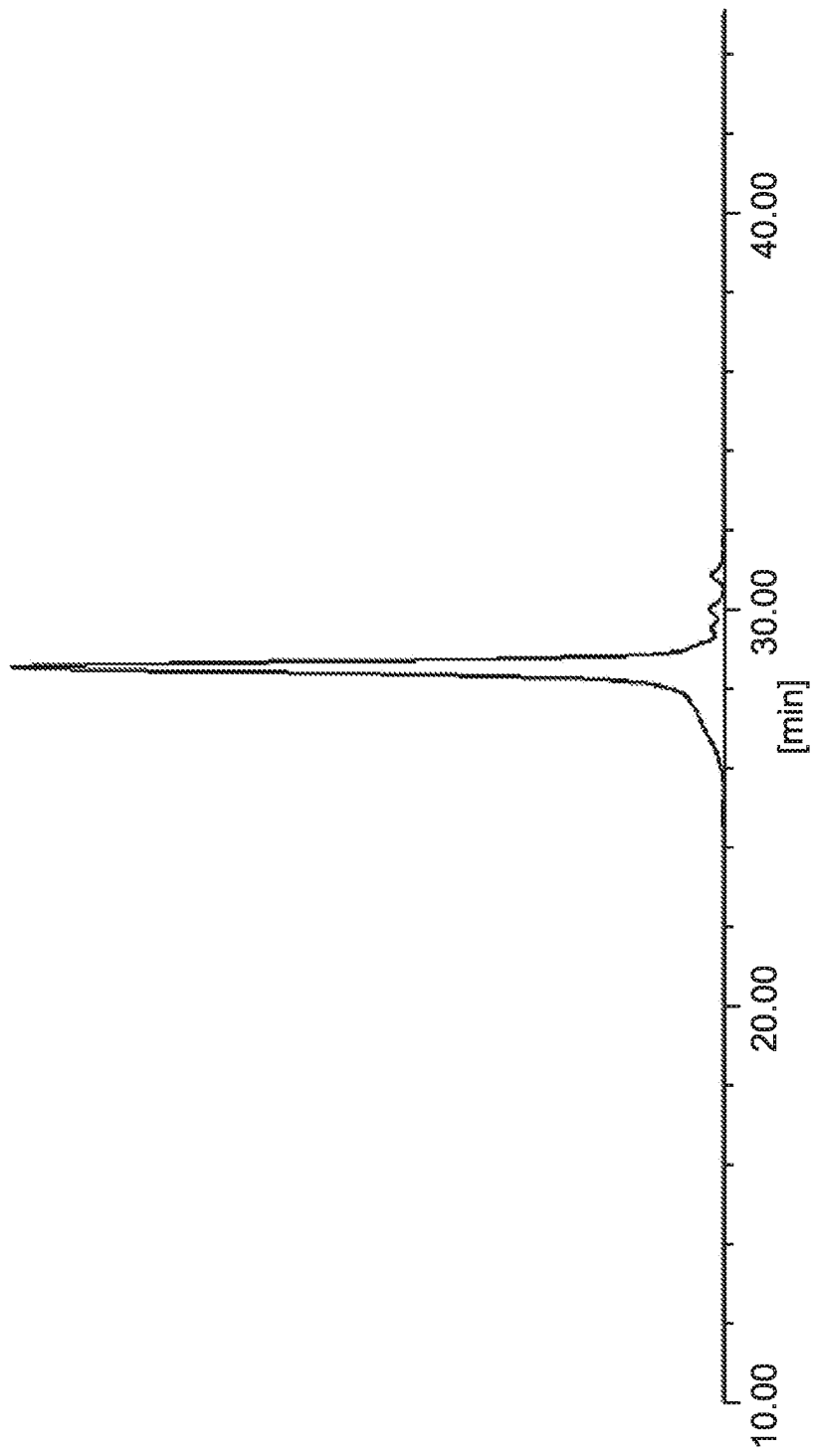
FIG. 5 is a GPC chart of a phenol resin (5) obtained in Example 5.

160 parts by mass of 1,6-dihydroxynaphthalene, 122 parts by mass of 4-hydroxybenzaldehyde, 290 parts by mass of 2-ethoxyethanol, and 1.7 parts by mass of 95% sulfuric acid were put into a flask equipped with a thermometer, a dropping funnel, a cooling tube, and a stirrer, and the resultant was heated to a temperature of 80° C., and then stirred for 8 hours. After the reaction was completed, 300 parts by mass of ethyl acetate and 160 parts by mass of ion exchanged water were added thereto, and then an aqueous layer having pH of 1 was separated from the underlayer by a separating funnel. An organic layer was washed with 160 parts by mass of ion exchanged water 7 times, and it was confirmed that pH of the separated aqueous layer was 4. After the organic layer was concentrated by heating under reduced pressure using evaporator, the organic layer was dried, thereby obtaining 247 parts by mass of a phenol resin (5) (yield of 93 mass %). A GPC chart of the phenol resin (5) is shown in FIG. 5. A peak of 1156 corresponding to the compound containing a phenolic hydroxy group (III) represented by Structural Formula (iii) below was detected from FD-MS spectrum. In addition, the content of the compound containing a phenolic hydroxy group (III) represented by Structural Formula (iii) below in the phenol resin (5) was 89%, which is calculated from the GPC chart.

[Chem. 9]

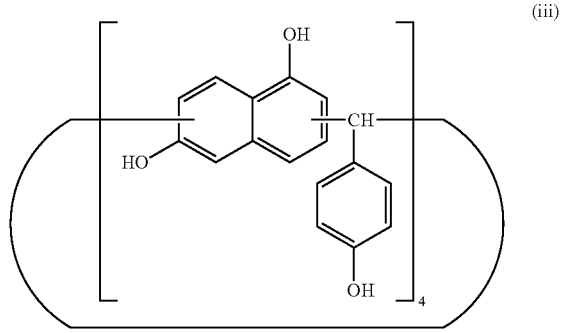

(iii)

Example 6 Isolation and Purification of Compound Containing a Phenolic Hydroxy Group (III)

Figure 6:
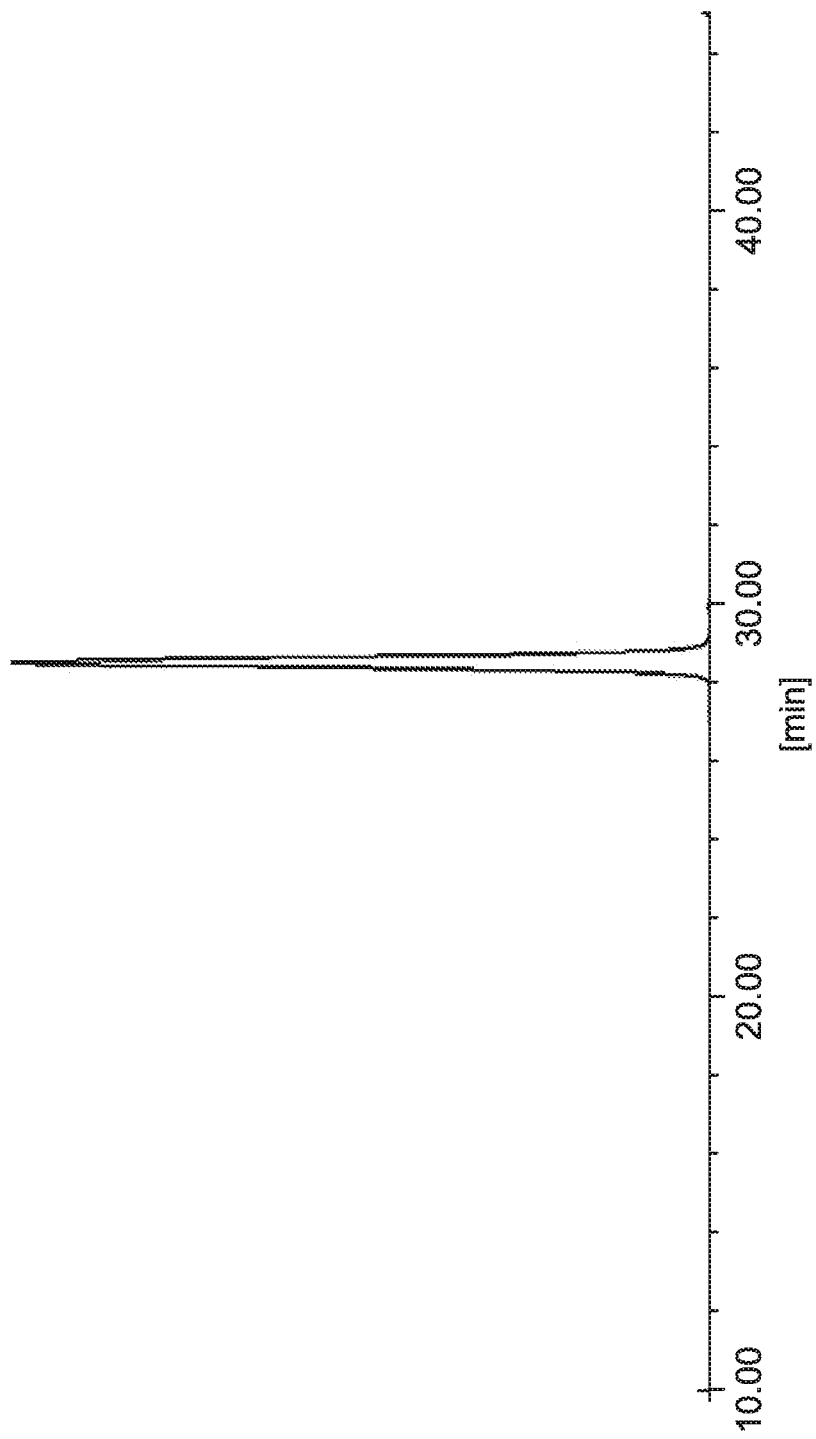
FIG. 6 is a GPC chart of a phenol resin (6) obtained in Example 6.
Figure 7:
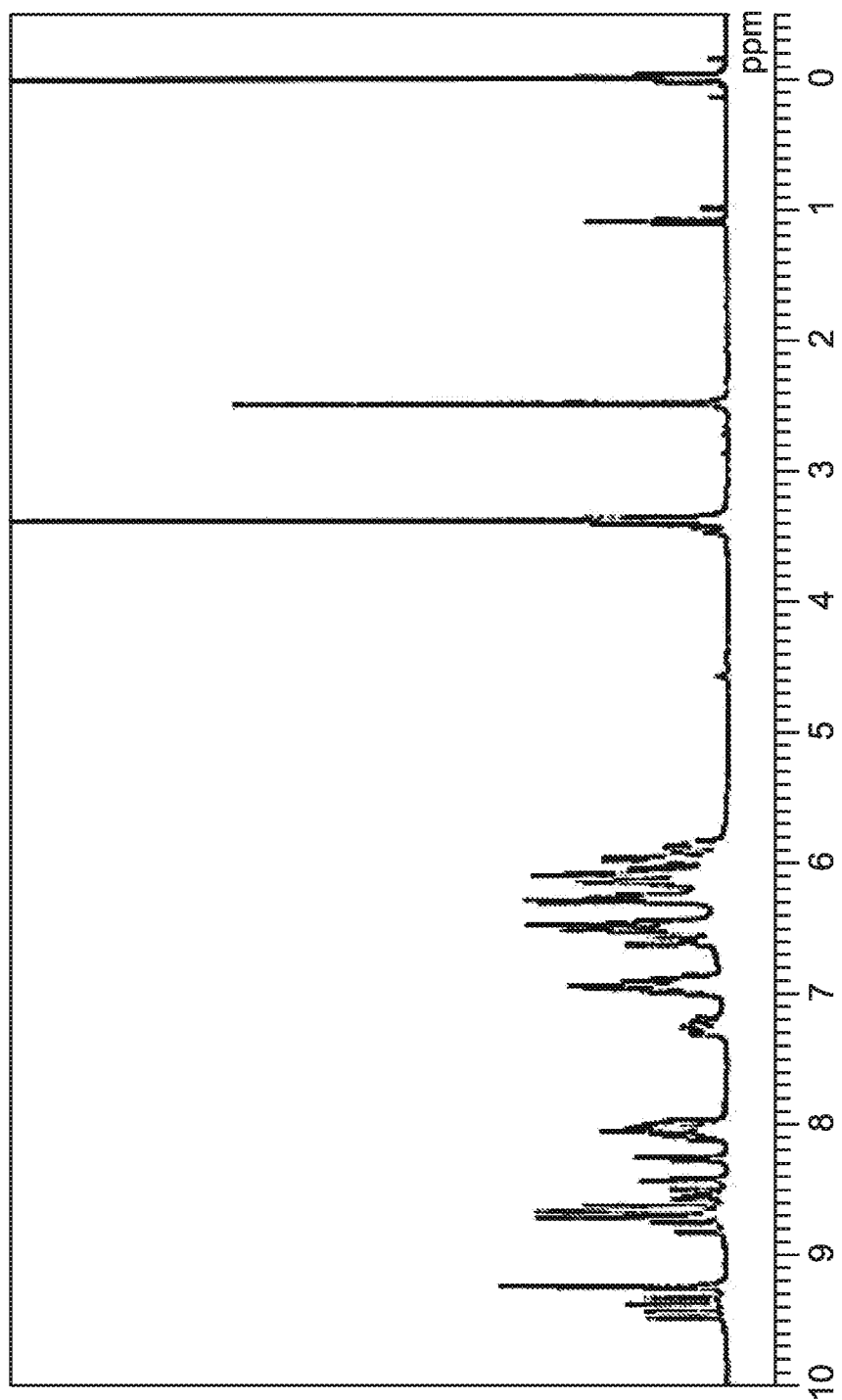
FIG. 7 is a 1H-NMR chart of the phenol resin (6) obtained in Example 6.
Figure 8:
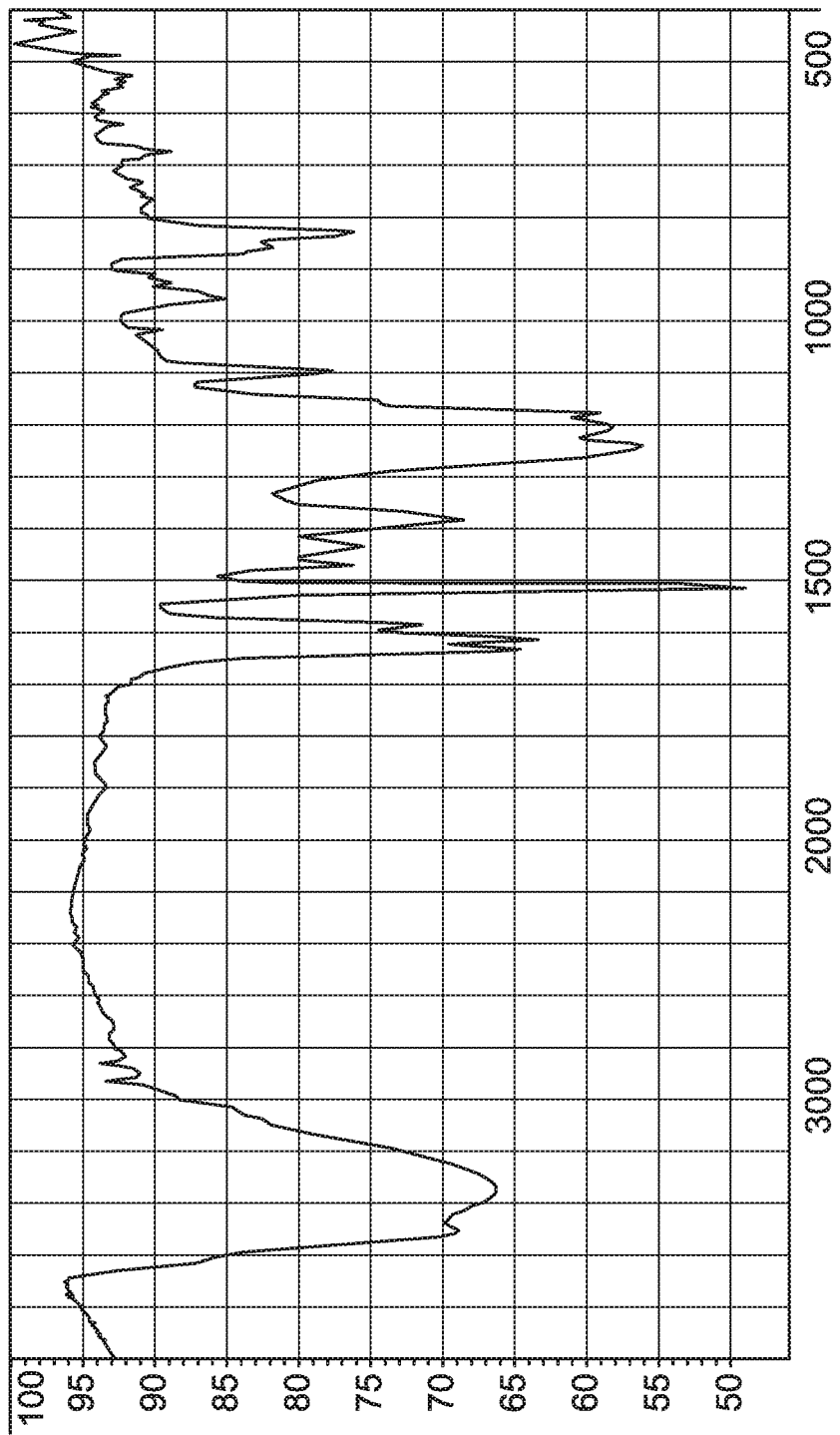
FIG. 8 is an IR chart of the phenol resin (6) obtained in Example 6.
Figure 9:
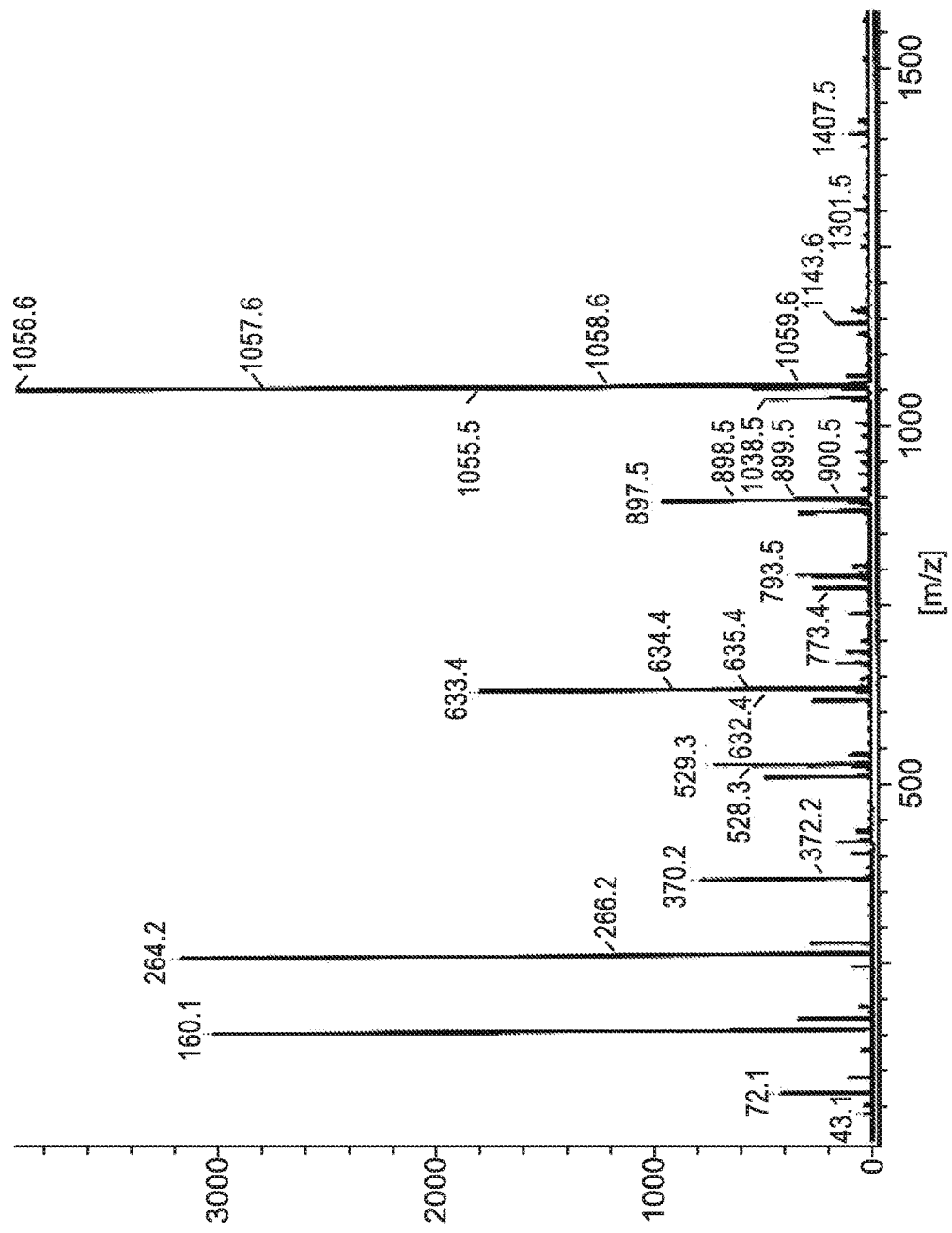
FIG. 9 is a FD-MS chart of the phenol resin (6) obtained in Example 6.

After 20 parts by mass of the phenol resin (5) obtained in Example 5 was dissolved in 20 parts by mass of methanol, the mixture was added dropwise to 60 parts by mass of ion exchanged water while stirring, and reprecipitation operation was performed. After the generated precipitate was filtered by a filter, and the obtained residue was fractionated, the residue was dried using a reduced-pressure drier, 12 parts by mass of the compound containing a phenolic hydroxy group (III) was isolated and purified. A GPC chart of the obtained compound containing a phenolic hydroxy group (1) is shown in FIG. 6, a 1H-NMR chart is shown in FIG. 7, an IR chart is shown in FIG. 8, and a FD-MS chart is shown in FIG. 9.

Example 7 Preparation of Phenol Resin (6)

Figure 10:
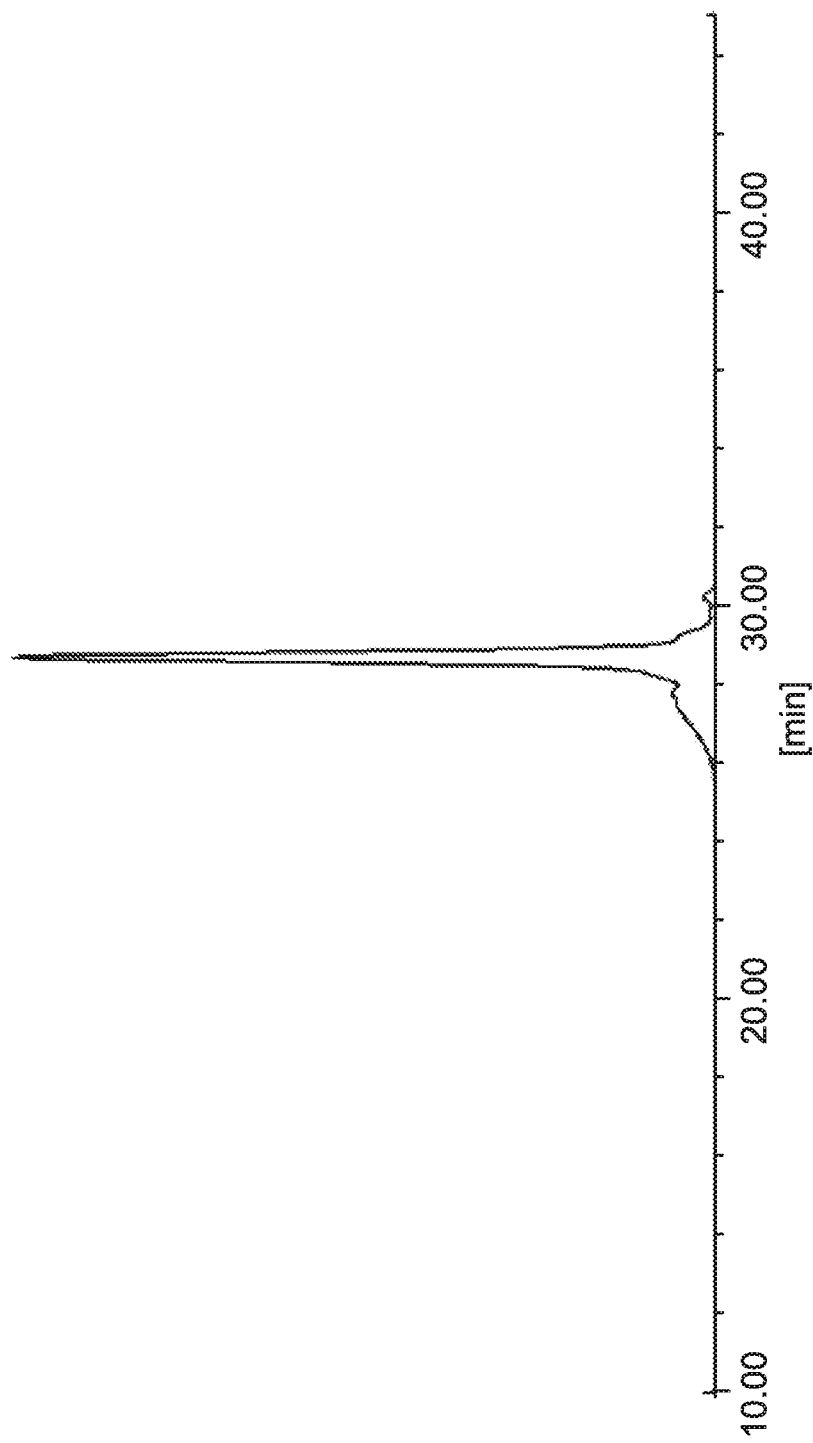
FIG. 10 is a GPC chart of a phenol resin (7) obtained in Example 7.

The operation was performed in the same manner as in Example 1 except that 122 parts by mass of salicylaldehyde was used instead of 4-hydroxybenzaldehyde in Example 5, thereby obtaining 252 parts by mass of a phenol resin (6) (yield of 95 mass %). A GPC chart of the phenol resin (6) is shown in FIG. 10. A peak of 1156 corresponding to the compound containing a phenolic hydroxy group (IV) represented by Structural Formula (iv) below was detected from FD-MS spectrum. In addition, the content of the compound containing a phenolic hydroxy group (IV) represented by Structural Formula (iv) above in the phenol resin (6) was 65%, which is calculated from the GPC chart.

[Chem. 10]

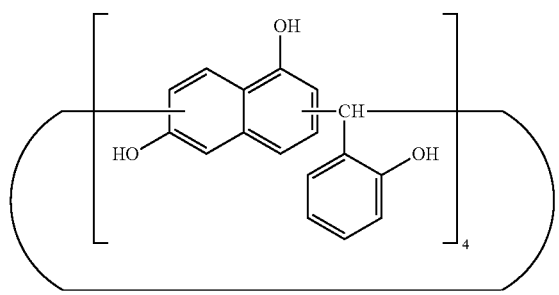

(iv)

Example 8 Isolation and Purification of Compound Containing a Phenolic Hydroxy Group (IV)

Figure 11:
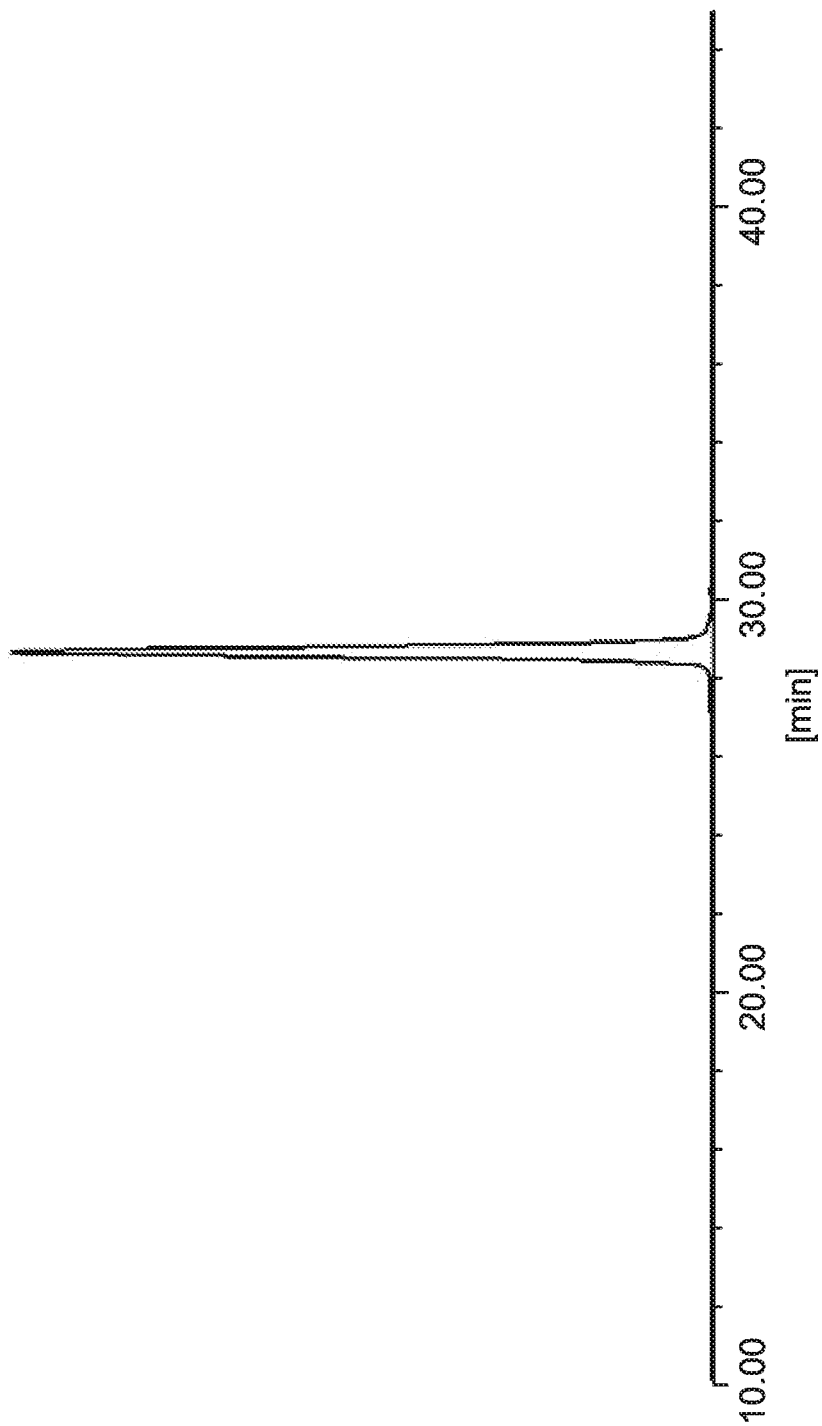
FIG. 11 is a GPC chart of a phenol resin (8) obtained in Example 8.
Figure 12:
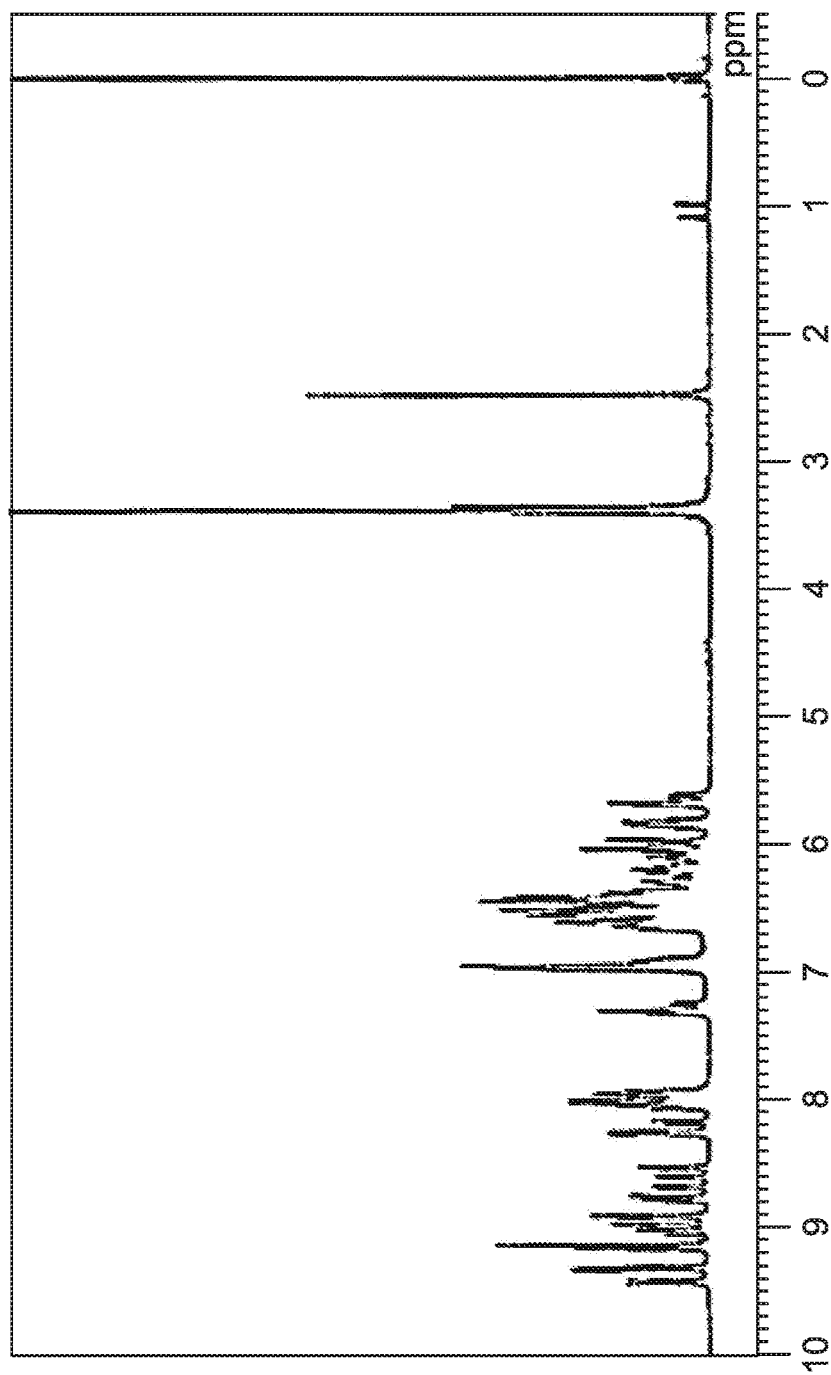
FIG. 12 is a 1H-NMR chart of the phenol resin (8) obtained in Example 8.
Figure 13:
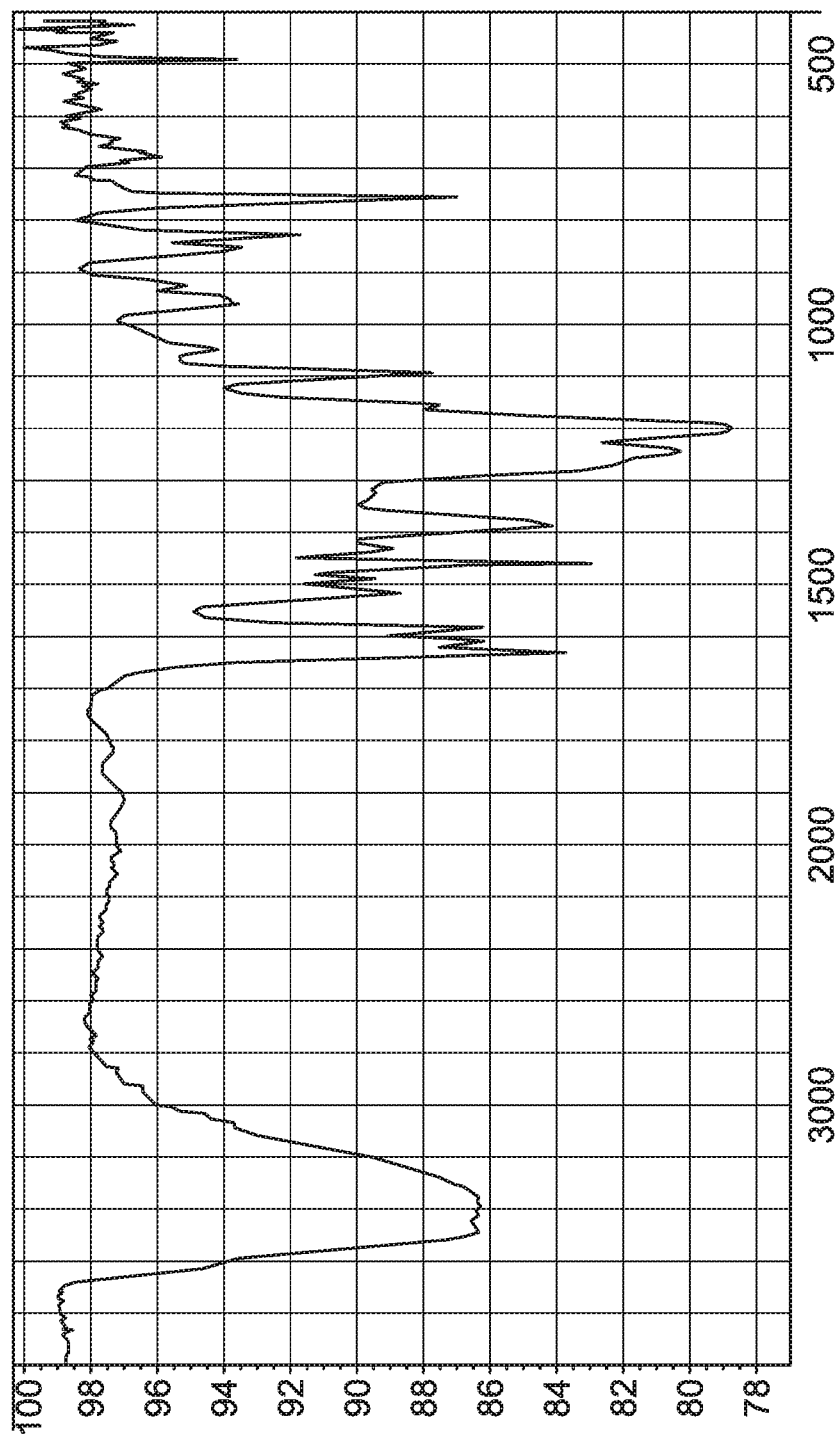
FIG. 13 is an IR chart of the phenol resin (8) obtained in Example 8.
Figure 14:
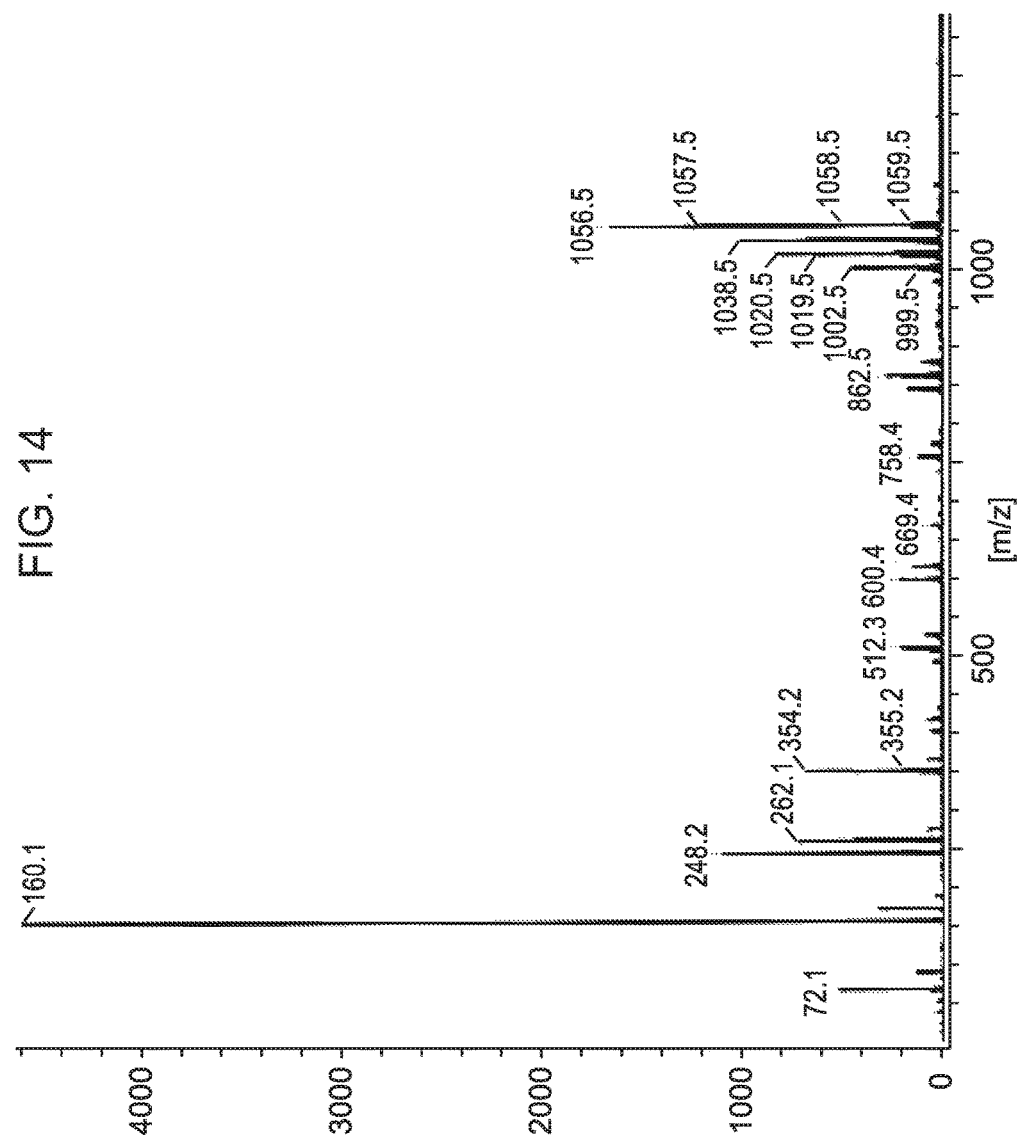
FIG. 14 is a FD-MS chart of the phenol resin (8) obtained in Example 8.

The operation was performed in the same manner as in Example 6 except that 20 parts by mass of the phenol resin (6) obtained in Example 7 was used, and 10 parts by mass of the compound containing a phenolic hydroxy group (IV) was isolated and purified. A GPC chart of the obtained compound containing a phenolic hydroxy group (IV) is shown in FIG. 11, a 1H-NMR chart is shown in FIG. 12, an IR chart is shown in FIG. 13, and a FD-MS chart is shown in FIG. 14.

Comparative Preparation Example 1 Preparation of Phenol Resin (1')

160 parts by mass (1.0 mole) of 1,6-dihydroxynaphthalene, 400 parts by mass of methyl isobutyl ketone, 96 parts by mass of water, and 27.7 parts by mass (0.85 moles) of 92% paraformaldehyde were put into a flask equipped with a thermometer, a cooling tube, and a stirrer, and the resultant was stirred at room temperature. Further, 4.8 parts by mass of paratoluenesulfonic acid aqueous solution of which the concentration was adjusted to 50% was added thereto, and the resultant was heated to a temperature of 80° C. while stirring and reacted for 2 hours. After the reaction was completed, the solution in the system was moved to a separating funnel, and an aqueous layer was separated from an organic layer and removed. Next, after washing was performed with water until the washing water is neutralized, and a solvent of the organic layer was removed by heating under reduced pressure, thereby obtaining 162 parts by mass of a phenol resin (1').

Comparative Preparation Example 2 Preparation of a Phenol Resin (2')

48 parts by mass (0.30 moles) of α-naphthol, 26 parts by mass (0.36 moles) of 42 mass % formaldehyde aqueous solution, 50 parts by mass of isopropyl alcohol, and 9.4 parts by mass (0.11 moles) of 48% sodium hydroxide were put into a flask equipped with a thermometer, a dropping funnel, a cooling tube, and a stirrer, and the resultant was stirred at room temperature while blowing nitrogen therein. After that, the resultant was heated to a temperature of 80° C. and stirred for 1 hour. After the reaction was completed, the resultant was neutralized by adding 8 parts by mass of primary sodium phosphate, and then cooled and a crystal was filtered out. After the crystal was washed with 50 parts by mass of water 3 times, the crystal was heated under reduced pressure and dried, thereby obtaining 47 parts by mass of a phenol resin (2').

Comparative Preparation Example 3 Preparation of Phenol Resin (3')

100 parts by mass of 9,9-bis(4-hydroxyphenyl)fluorene, 100 parts by mass of propylene glycol monomethyl ether acetate, and 50 parts by mass of paraformaldehyde were put into a reaction apparatus equipped with a condenser, a thermometer, and a stirring apparatus, 2 parts by mass of an oxalic acid was added thereto, and the resultant was heated to a temperature of 120° C. while dehydrating and reacted for 5 hours, thereby obtaining 98 parts by mass of a phenol resin (3') composed of a structural unit represented by formula below.

[Chem. 11]

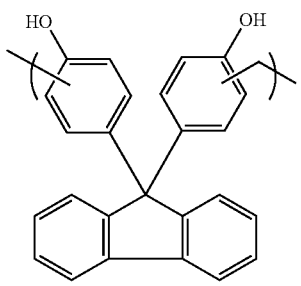

Examples 9 to 14 and Comparative Examples 1 to 3

With respect to each of the phenol resins (1) to (4), the compounds containing a phenolic hydroxy group (III) and (IV), and the phenol resins (1') to (3') obtained previously, solvent solubility and heat resistance were evaluated according to the following manner. The results are shown in Table 1.

<Evaluation of Solvent Solubility>

20 parts by mass of the phenol resin or the compound containing a phenolic hydroxy group, and 100 parts by mass of propylene glycol monomethyl ether acetate (hereinafter, shortly referred to as "PGMEA") were blended with each other and stirred by a shaking apparatus at a temperature of 25° C. After stirring, a state of the solvent within the container was visually confirmed, a uniform and transparent state was evaluated as A, and a state in which a solid content was precipitated or deposited was evaluated as C.

<Evaluation of Heat Resistance>

With respect to each of the phenol resins or the compounds containing a phenolic hydroxy group, a weight reduction in a case where the resin and the compound were heated at a constant rate under the conditions described below was measured using a simultaneous thermogravimetric and differential thermal analyzer (TG/DTA), and an initial temperature of thermal decomposition was obtained. As the initial temperature of thermal decomposition becomes higher, heat resistance becomes more excellent.

Measuring apparatus: TG/DTA 6200 manufactured by Seiko Instruments Inc.

Measuring range: RT to 400° C.

Temperature rising rate: 10° C./min

Atmosphere: Nitrogen

TABLE 1

| | Example 9 | Example 10 | Example 11 | Example 12 | Example 13 | Example 14 | Comparative Example 1 | Comparative Example 2 | Comparative Example 3 |
|---|---|---|---|---|---|---|---|---|---|
| Phenol resin or Compound containing a phenolic hydroxy group | (1) | (2) | (3) | (4) | (III) | (IV) | (1') | (2') | (3') |
| Solvent solubility | A | A | A | A | A | A | A | C | A |
| Initial temperature of thermal decomposition (° C.) | 186 | 185 | 183 | 194 | 192 | 197 | 151 | 177 | 173 |

Evaluation of Photosensitive Composition

With respect to each of the phenol resins (1) to (4), the compounds containing a phenolic hydroxy group (III) and (IV), and the phenol resin (1') previously obtained, a photosensitive composition was prepared according to the following manner, and tests for evaluating optical sensitivity and resolution were performed. The results are shown in Table 2.

<Evaluation of Optical Sensitivity>

Formation of Coating 16 parts by mass of the phenol resin or the compound containing a phenolic hydroxy group was dissolved in 80 parts by mass of PGMEA, 4 parts by mass of a photosensitizer ("P-200" manufactured by Toyo Gosei Co., Ltd.) was further added thereto, and the resultant was mixed and filtered by a 0.2 μm membrane filter, thereby obtaining a photosensitive composition (a). In the same manner, 20 parts by mass of the compound containing a phenolic hydroxy group or the phenol resin was dissolved in 80 parts by mass of PGMEA, and the resultant was filtered by a 0.2 μm membrane filter, thereby obtaining a composition (b) containing no photosensitizer.

Each of the obtained compositions (a) and (b) were applied to a silicon wafer having a diameter of 5 inches using a spin coater, and then dried at a temperature of 110° C. for 60 seconds, thereby obtaining coatings (A) and (B) having a thickness of about 1 μm.

Photosensitizer "P-200" manufactured by Toyo Gosei Co., Ltd.: Condensate of 1 mole of 4,4'-[1-[4-[1-(4-hydroxyphenyl)-1-methylethyl]phenyl]ethylidene]bisphenol and 2 moles of 1,2-naphthoquinone-2-diazido-5-sulfonyl chloride Measurement of Alkali Solution Dissolution Rate The obtained coatings (A) and (B) were immersed in an alkali solution (2.38 mass % tetramethylammonium hydroxide aqueous solution) for 60 seconds, the thickness of each of the coatings after immersion was measured by a film thickness meter ("F-20" manufactured by Filmetrics Japan, Inc.), and an alkali dissolution rate (ADR) was evaluated. As the alkali solution dissolution rate of the coating (A) becomes lower and the alkali dissolution rate of the coating (B) becomes higher, the optical sensitivity of the resist composition becomes more excellent.

<Evaluation of Resolution>

Formation of Coating 16 parts by mass of the phenol resin or the compound containing a phenolic hydroxy group was dissolved in 80 parts by mass of PGMEA, 4 parts by mass of a photosensitizer ("P-200" manufactured by Toyo Gosei Co., Ltd.) was further added thereto, and the resultant was mixed and filtered by a 0.2 μm membrane filter, thereby obtaining a resist composition. The obtained photosensitive resin composition was applied to a silicon wafer having a diameter of 5 inches using a spin coater, and then dried at a temperature of 110° C. for 60 seconds, thereby preparing a silicon wafer with a coating.

Evaluation of Resolution

A photomask was laid on a coating surface of the obtained silicon wafer with a coating and the silicon wafer was irradiated at an intensity of 100 mJ/cm$^2$ with multilight (g•h•i rays) manufactured by USHIO INC. to expose to light. After the light-exposed silicon wafer was immersed in an alkali solution (2.38 mass % tetramethylammonium hydroxide aqueous solution) for 60 seconds, the pattern surface was washed with pure water, and spin-dried by a spin coater, and then dried at a temperature of 100° C. for 60 seconds. A state of the resist pattern on the obtained silicon wafer was confirmed by a laser microscope ("VK-8500" manufactured by KEYENCE CORPORATION) and evaluated.

A: Resolution was performed at a L/S of 5 μm.
C: Resolution was not performed at a L/S of 5 μm.

TABLE 2

|  | Example 9 | Example 10 | Example 11 | Example 12 | Example 13 | Example 14 | Comparative Example 1 |
|---|---|---|---|---|---|---|---|
| Phenol resin or Compound containing a phenolic hydroxy group | (1) | (2) | (3) | (4) | (III) | (IV) | (1') |
| Alkali dissolution rate of coating (A) with photosensitizer (nm/sec) | 0.8 | 1.0 | 0.7 | 0.4 | 0.1 | 0.1 | 41 |
| Alkali dissolution rate of coating (B) without photosensitizer (nm/sec) | >200 | >200 | >200 | >200 | >200 | >200 | >200 |
| Resolution | A | A | A | A | A | A | C |

Evaluation of Curable Composition

With respect to each of the phenol resins (1) and (4), the compounds containing a phenolic hydroxy group (III) and (IV), and the phenol resin (3') previously obtained, a curable composition was prepared according to the following manner, and the tests for evaluating alkali solution dissolution rate and dry etching resistance were performed. The results are shown in Table 3.

<Measurement of Alkali Solution Dissolution Rate>

Formation of Coating 20 parts by mass of the compound containing a phenolic hydroxy group or the phenol resin and 1 part by mass of a curing agent ("1,3,4,6-tetrakis(methoxymethyl)glycoluril" manufactured by TOKYO CHEMICAL INDUSTRY CO., LTD.) were dissolved in 100 parts by mass of PGMEA and filtered by a 0.2 μm membrane filter, thereby obtaining a curable composition. The composition was applied to a silicon wafer having a diameter of 5 inches using a spin coater, and then dried at a temperature of 110° C. for 60 seconds, thereby obtaining a silicon wafer with a coating having a thickness of about 1 μm.

Measurement of Alkali Solution Dissolution Rate

The obtained silicon wafer with a coating was immersed in an alkali solution (2.38 mass % tetramethylammonium hydroxide aqueous solution) for 60 seconds, the thickness of the coating after immersion was measured by a film thickness meter ("F-20" manufactured by Filmetrics Japan, Inc.), and an alkali dissolution rate (ADR) was evaluated.

<Evaluation of Dry Etching Resistance>

Formation of Coating 20 parts by mass of the phenol resin or the compound containing a phenolic hydroxy group and 1 part by mass of a curing agent ("1,3,4,6-tetrakis(methoxymethyl)glycoluril" manufactured by TOKYO CHEMICAL INDUSTRY CO., LTD.) were added to 100 parts by mass of PGMEA and mixed, and the mixture was filtered by a 0.2 μm membrane filter, thereby obtaining a curable composition.

Evaluation of Dry Etching Resistance

The obtained composition for a resist underlayer coating was applied to a silicon wafer having a diameter of 5 inches using a spin coater, and then heated within a hot plate having an oxygen concentration of 20 volume % at a temperature of 180° C. for 60 seconds. Further, the composition was heated at a temperature of 350° C. for 120 seconds, and a silicon wafer with a resist underlayer coating having a coating thickness of 0.3 μm was obtained. The formed resist underlayer coating was subjected to etching treatment under the condition of CF$_4$/Ar/O$_2$ (CF$_4$: 40 mL/min, Ar: 20 mL/min, O$_2$: 5 mL/min, pressure: 20 Pa, RF power: 200 W, treatment time: 40 seconds, and temperature: 15° C.) using an etching equipment ("EXAM" manufactured by Shinko Seiki Co., Ltd.). At this time, the coating thickness before and after the etching treatment was measured, an etching rate was calculated, and etching resistance was evaluated. The evaluation standard is as follows.

A: Etching rate is 150 nm/min or less
C: Etching rate exceeds 150 nm/min

TABLE 3

|  | Example 9 | Example 12 | Example 13 | Example 14 | Comparative Example 3 |
|---|---|---|---|---|---|
| Phenol resin or compound containing a phenolic hydroxy group | (1) | (4) | (III) | (IV) | (3') |
| Alkali dissolution rate of coating before curing (nm/sec) | >200 | >200 | >200 | >200 | 32 |
| Dry etching resistance | A | A | A | A | C |

The invention claimed is:

1. A calix[2-10]arene compound which is obtained by reacting a 1,6-dihydroxynaphthalene compound with formaldehyde in the presence of a basic catalyst; wherein the 1,6-dihydroxynaphthalene is unsubstituted or substituted by any of alkyl, alkoxy, aryl, aralkyl or halogen.

2. A photosensitive composition comprising the calix[2-10]arene compound according to claim 1 and a photosensitizer.

3. A resist coating formed by coating the photosensitive composition of claim 2.

4. A curable composition comprising the calix[2-10]arene compound according to claim 1 and a curing agent.

5. A cured product obtained by curing the curable composition of claim 4.

6. A resist underlayer coating formed by coating and curing the curable composition of claim 4.

7. A calix[2-10]arene compound which is obtained by reacting a 1,6-dihydroxynaphthalene compound with an aliphatic aldehyde compound having 2 or more carbon atoms or an aromatic aldehyde compound, in the presence of an acid catalyst; wherein the 1,6-dihydroxynaphthalene is unsubstituted or substituted by any of alkyl, alkoxy, aryl, aralkyl or halogen.

8. A photosensitive composition comprising the calix[2-10]arene compound according to claim 4 and a photosensitizer.

9. A resist coating formed by coating the photosensitive composition of claim 8.

10. A curable composition comprising the calix[2-10]arene compound according to claim 7 and a curing agent.

11. A cured product obtained by curing the curable composition of claim 10.

12. A resist underlayer coating formed by coating and curing the curable composition of claim 10.

* * * * *